(12) United States Patent
Lazzarini et al.

(10) Patent No.: US 7,351,687 B2
(45) Date of Patent: **\*Apr. 1, 2008**

(54) ANTIBIOTIC 107891, ITS FACTORS A1 AND A2, PHARMACEUTICALLY ACCEPTABLE SALTS AND COMPOSITIONS, AND USE THEREOF

(75) Inventors: Ameriga Lazzarini, Legnano (IT); Luciano Gastaldo, Pogliano Milanese (IT); Gianpaolo Candiani, Gorgonzola (IT); Ismaela Ciciliato, Busto Arsizio (IT); Daniele Losi, Rovellasca (IT); Flavia Marinelli, Milan (IT); Enrico Selva, Gropello Cairoli (IT); Franco Parenti, Lainate (IT)

(73) Assignee: Vicuron Pharmaceuticals, Inc., King of Prussia, PA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 11/045,628

(22) Filed: Jan. 26, 2005

(65) Prior Publication Data

US 2005/0233952 A1 Oct. 20, 2005

Related U.S. Application Data

(63) Continuation-in-part of application No. 11/035,296, filed on Jan. 12, 2005, which is a continuation-in-part of application No. 10/521,336, filed as application No. PCT/EP2004/007658 on Jul. 12, 2004.

(30) Foreign Application Priority Data

Jul. 18, 2003 (EP) ................... 03016306

(51) Int. Cl.
*A61K 38/04* (2006.01)
(52) U.S. Cl. ........................................................ 514/2
(58) Field of Classification Search ............... None
See application file for complete search history.

(56) References Cited

U.S. PATENT DOCUMENTS 6,551,591 B1 4/2003 Lee

FOREIGN PATENT DOCUMENTS

EP 0 592 835 4/1994
JP 59 198982 11/1984

OTHER PUBLICATIONS

Database WPI Section Ch, Week 198451, Derwent Publications Ltd, London, GB, AN 1984-316058.
Hayakawa, M. et al. "Distribution of antibiotic-producing Microbispora strains in soils with different pHs" ACTINOMYCETES 6(3): 75-79 (1995).
Lazzarini, A. et al. "Rare genera of actinomycetes as potential producers of new antibiotics" antonie Van Leeuwenhoek 78(3-4): 399-405 (Dec. 2000).
McAuliffe, O. et al. "Lantibiotics: structure, biosynthesis and mode of action" FEMS Microbiology Reviews 25(3): 285-308 (May 2001).
Sahl, H-G. et al. "Lantibiotics : Biosynthesis and Biological Activities of Uniquely Modified Peptides from Gram-Positive Bacteria" Ann. Rev. Microbiol. 52:41-79 (1998).
Xu, S-Z. et al. "Isolation of the genus Microbispora from soil of China" Weishengu Xuebao 19(3): 255-58 (1979).

*Primary Examiner*—Cecilia J. Tsang
*Assistant Examiner*—Christina M. Bradley
(74) *Attorney, Agent, or Firm*—John Kappos; Charles W. Ashbrook; John H. Engelmann

(57) ABSTRACT

The invention relates to an antibiotic substance of microbial origin, arbitrarily denominated antibiotic 107891 which is produced by fermentation of *Microbispora* sp. ATCC PTA-5024, the pharmaceutically acceptable salts and compositions thereof, and their use as an antibacterial agent having inhibitory activity versus susceptible microbes. Antibiotic 107891, which is a complex comprising two Factors, denominated Factors A1 and A2, has a peptide structure containing lanthionine and methyllanthionine as constituents which are typical characteristics of the antibiotics of the lantibiotics group. Antibiotic 107891 and its Factors A1 and A2 show a good antibacterial activity against Gram-positive bacteria including methicillin resistant and vancomycin resistant strains, and is active also against some Gram-negative bacteria such as *M. catharralis*, *Neisseria* species and *H. influenzae* and Mycobacteria.

13 Claims, 18 Drawing Sheets

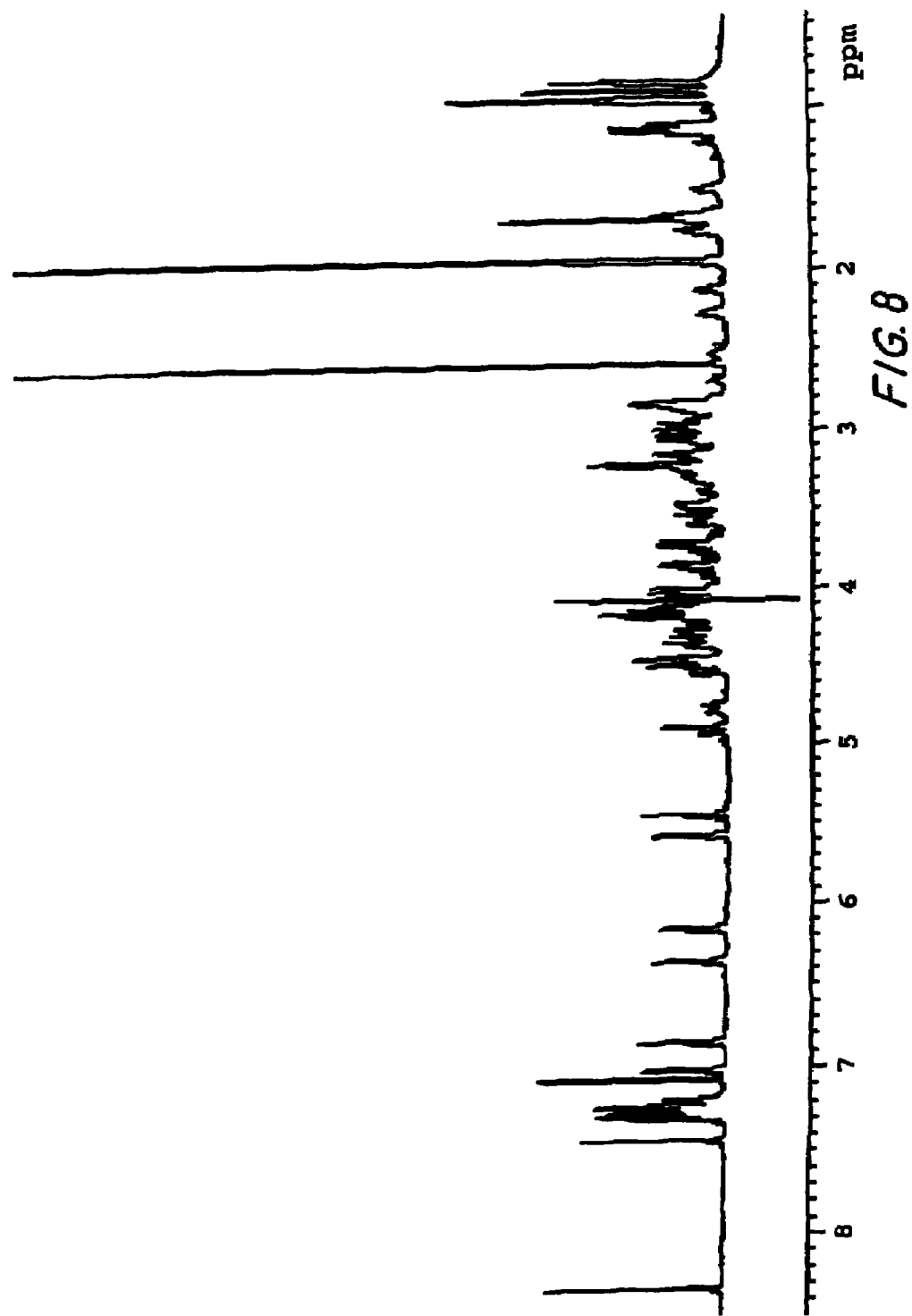

SEQUENCE LISTING

<160> NUMBER OF SEQ ID NOS: 1

<210> SEQ ID NO 1
<211> LENGTH: 1443
<212> TYPE: DNA
<213> ORGANISM: Microbispora sp. ATCC PTA-5024

<400> SEQUENCE: 1

```
gacgaacgct ggcggcgtgc ttaacacatg caagtcgagc ggaaaggccc ttcggggtac      60
tcgagcggcg aacgggtgag taacacgtga gtaacctgcc cctgactctg ggataagcct     120
gggaaaccgg gtctaatacc ggatatgaca catggtcgca tgagcggtgt gtggaaagtt    180
ttttcggttg gggatgggct cgcggcctat cagcttgttg gtggggtgat ggcctaccaa     240
ggcgacgacg ggtagccggc ctgagagggc gaccggccac actgggactg agacacggcc     300
cagactccta cgggaggcag cagtggggaa tattgcgcaa tgggcggaag cctgacgcag     360
cgacgccgcg tgggggatga cggccttcgg gttgtaaacc tctttcagca gggacgaagt     420
tgacgtgtac ctgtagaaga agcgccggct aactacgtgc cagcagccgc ggtaatacgt     480
agggcgcaag cgttgtccgg aattattggg cgtaaagagc tcgtaggtgg cttgttgcgt     540
ctgccgtgaa agcccgtggc ttaactacgg gtctgcggtg gatacgggca ggctagaggc     600
tggtagggc aagcggaatt cctggtgtag cggtgaaatg cgcagatatc aggaggaaca     660
ccggtggcga aggcggcttg ctgggccagt tctgacgctg aggagcgaaa gcgtggggag     720
cgaacaggat tagataccct ggtagtccac gctgtaaacg ttgggcgcta ggtgtggggg     780
tcttccacga ttcctgtgcc gtagctaacg cattaagcgc cccgcctggg gagtacggcc     840
gcaaggctaa aactcaaagg aattgacggg ggcccgcaca agcggcggag catgttgctt     900
aattcgacgc aacgcgaaga accttaccaa ggtttgacat acaccggaaa gctctggaga     960
cagggccctc ctttggactg gtgtacaggt ggtgcatggc tgtcgtcagc tcgtgtcgtg    1020
agatgttggg ttaagtcccg caacgagcgc aaccccttgtt ccatgttgcc agcacgccct    1080
ttggggtggt ggggactcat gggagactgc cggggtcaac tcggaggaag gtggggatga    1140
cgtcaagtca tcatgcccct tatgtcttgg gctgcaaaca tgctacaatg gtcggtacag    1200
agggttgcga tgccgtgagg tggagcgaat ccctaaaagc cggtctcagt tcggattggg    1260
gtctgcaact cgaccccatg aagtcggagt cgctagtaat cgcagatcag caacgctgcg    1320
gtgaatacgt tcccgggcct tgtacacacc gcccgtcacg tcacgaaagt cggcaacacc    1380
cgaagcccgt ggcccaacca cttgtggggg gagcggtcga aggtggggct ggcgattggg    1440
acg                                                                  1443
```

ANTIBIOTIC 107891, ITS FACTORS A1 AND A2, PHARMACEUTICALLY ACCEPTABLE SALTS AND COMPOSITIONS, AND USE THEREOF

This application is a continuation-in-part of U.S. application Ser. No. 11/035,296, filed Jan. 12, 2005, which is a continuation-in-part of U.S. application Ser. No. 10/521,336, filed on Jan. 11, 2005, which is a § 371 national filing of PCT/EP2004/007658, filed on Jul. 12, 2004, which claims priority to EP Application No. 03016306.7, filed Jul. 18, 2003, all of which are hereby expressly incorporated by reference in their entirety.

The present invention concerns an antibiotic substance of microbial origin, arbitrarily denominated antibiotic 107891, which is a complex comprising Factors A1 and A2, the pharmaceutical acceptable salts thereof, pharmaceutical compositions thereof and their use as an antibacterial agent.

Another object of the present invention is a process for preparing antibiotic 107891 which includes culturing *Microbispora* sp. 107891 (hereinafter identified as *Microbispora* sp. ATCC PTA-5024) or a variant or mutant thereof maintaining the ability to produce said antibiotic, recovering the antibiotic of the invention from the mycelium and/or from the fermentation broth, isolating the pure substance by chromatographic means and separating Factors A1 and A2.

Antibiotic 107891 is a novel antimicrobial agent with a peptide structure containing lanthionine and methyllanthionine as constituents. These are the typical characteristics of lantibiotics and, in particular, of the subgroup acting primarily on cell wall biosynthesis.

Lantibiotics are peptides, which contain the thioether amino acid lanthionine as well as several other modified amino acids (H. G. Sahl and G. Bierbaum, (1998) "Lantibiotics: biosynthesis and biological activities of uniquely modified peptides from gram-positive bacteria", Ann. Rev. Microbiol. 52:41-79). The majority of known lantibiotics have antibacterial activity, although some have been reported as active on different pharmacological targets. The antibacterial lantibiotics can be broadly divided into two groups on the basis of their structures: type-A lantibiotics are typically elongated, amphiphilic peptides, while type-B lantibiotics are compact and globular (O. McAuliffe, R. P. Ross and C. Hill, (2001): "Lantibiotics: structure, biosynthesis and mode of action", FEMS Microb. Rev. 25: 285-308). Nisin is the typical representative of type A lantibiotic, whereas actagardine (gardimycin) and mersacidin belong to the type B lantibiotic subclass. Both nisin-type and mersacidin-type lantibiotics interact with the membrane-bound peptidoglycan precursors lipid II, although the two classes differ in the effects they produce in the bacterial proliferation process. Nisin-type lantibiotics primarily kill bacteria by permeabilization of the cytoplasmic membrane (H. Brotz, M. Josten, I. Wiedemann, U. Schneider, F. Gotz, G. Bierbaum and H. G. Sahl, (1998): "Role of lipid-bound peptidoglycan precursors in the formation of pores by nisin, epidermin and other lantibiotics", Mol. Microbiol. 30:317-27), whereas mersacidin-type lantibiotics primary kill the bacterial cell by inhibiting the cell wall biosynthesis (H. Brotz, G. Bierbaum, K. Leopold, P. E. Reynolds and H. G. Sahl, (1998): "The lantibiotic mersacidin inhibits peptidoglycan synthesis by targeting lipid II", Antimicrob Agents Chemother. 42:154-60).

Two antibiotics produced by *Microbispora corallina* strain NRRLL 30420, identified as antibiotic MF-BA-1768$\alpha_1$ and MF-BA-1768$\beta_1$, respectively, are described in U.S. Pat. No. 6,551,591 B1. The physico-chemical data reported in the above-identified patent (e.g. mass spectroscopy data, molecular weight, content of aminoacids) and comparison of the retention times in LC-MS experimental analyses clearly show that the antibiotic 107891 complex as well as its components Factor A1 and Factor A2 are chemical entities distinct from antibiotics MF-BA 1768$\alpha_1$ and MF-BA-1768$\beta_1$.

EP 0592835A2 describes antitumor antibiotics BU-4803TA$_1$, A$_2$, B, C$_1$, C$_2$ and D. Antibiotics BU-4803TA$_1$ A$_2$, and B are recovered from the fermentation broth of *Microbispora* ATCC 55327 (AA 9966) while antibiotics BU4803TC$_1$, C$_2$ and D are products of transformation of antibiotic BU 4803TA$_1$, A$_2$ and B, respectively, when these products are stored in dimethyl sulfoxide. The physicochemical data reported in EP 0592 835 A for the above antibiotics (e.g. aspect, U.V. absorbtion, molecular weight, antitumor activity, clearly show that they are chemical substances distinct from antibiotic 107891 complex and its Factors A1 and A2.

Strain and Fermentation

*Microbispora* sp. 107891 was isolated in the environment and deposited on Feb. 27, 2003 with the American Type Culture Collection (ATCC), 10801 University Blvd, Manassas Va., 20110-2209 U.S.A., under the provision of the Budapest Treaty. The strain was accorded accession number PTA-5024.

The production of antibiotic 107891 is achieved by cultivating a *Microbispora* sp. strain capable of producing it, i.e. *Microbispora* sp. ATCC PTA-5024 or a variant or mutant thereof maintaining the ability to produce said antibiotic; isolating the resulting antibiotic from the whole culture broth and/or from the separated mycelium and/or from the filtered fermentation broth; and purifying the isolated antibiotic by chromatographic means. In any case, it is preferred to produce antibiotic 107891 under aerobic conditions in an aqueous nutrient medium containing easy assimilable sources of carbon, nitrogen, and inorganic salts. Many of the nutrient media usually employed in the fermentation field can be used, however certain media are preferred.

Preferred carbon sources are sucrose, fructose, glucose, xylose, and the like. Preferred nitrogen sources are soybean meal, peptone, meat extract, yeast extract, tryptone, aminoacids, hydrolized casein and the like. Among the inorganic salts which can be incorporated in the culture media, there are the customary soluble salts capable of yielding sodium, potassium, iron, zinc, cobalt, magnesium, calcium, ammonium, chloride, carbonate, sulphate, phosphate, nitrate, and the like ions.

Preferably, the strain producing antibiotic 107891 is pre-cultured in a fermentation tube or in a shake flask, then the culture is used to inoculate jar fermentors for the production of substantial quantities of substances. The medium used for the pre-culture can be the same as that employed for larger fermentations, but other media can also be employed. The strain producing antibiotic 107891 can be grown at temperature between 17° C. and 37° C., optimal temperatures being around 28-30° C.

During the fermentation, antibiotic 107891 production can be monitored by bioassay on susceptible microorganisms and/or by HPLC analyses. Maximum production of antibiotic 107891 generally occurs after circa 90 hours and before the 200 hours of fermentation.

Antibiotic 107891 is produced by cultivating *Microbispora* sp. ATCC PTA-5024 or a variant or mutant thereof capable of producing antibiotic 107891, and it is found in the culture broths and/or in the mycelium.

In this description and claims the term "antibiotic 107891", unless otherwise specified, identifies the antibiotic 107891 complex comprising Factors A1 and A2.

Morphological Characteristics of *Microbispora* sp. ATCC PTA-5024

*Microbispora* sp. ATCC PTA-5024 grows well on various standard solid media. Microscopic dimensions were measured using the culture grown on humic acid-Trace Salts Agar (composition in g/l: humic acid 0.5, $FeSO_4*7H_2O$ 0.001, $MnCl_2*4H_2O$ 0.001, $ZnSO_4*7H_2O$ 0.001, $NiSO_4*6H_2O$ 0.001, MOPS 2, agar 20) added with 1 ml/l of vitamins solution (thiamine hydrochloride 25 mg/l, calcium pantotenate 250 mg/l, nicotinic acid 250 mg/l, biotin 0.5 mg/l, riboflavin 1.25 g/l, cyanocobalamin 6.25 mg/l, paraminobenzoic acid 25 mg/l, folic acid 500 mg/l, pyridoxal hydrochloride 500 mg/l).

In liquid culture (V6 medium, composition in g/l: dextrose 22, meat extract 5, yeast extract 5, casein 3, NaCl 1.5) no fragmentation of the mycelium is observed after 6 days of growth at 28° C. Microscopic examination on Humic acid-Trace Salts Agar (after 21 days of incubation at 28° C.) reveals a branched, un-fragmented substrate mycelium and a monopodially branched aerial mycelium; many long, straight and poorly branched aerial hyphae are also visible. Characteristic longitudinal pairs of spores are borne by short sporophores laterally arising from branches or directly from the main aerial hyphae. Spores are globose and non-motile. Sporangium-like bodies or other particular structures are not observed.

Cultural Characteristics of *Microbispora* sp. ATCC PTA-5024

*Microbispora* sp. ATCC PTA-5024 was grown for six days in AF/MS liquid medium (see Example 1) at 28° C. and 200 rpm, then transferred (5% inoculum) to a new AF/MS liquid medium and grown for further 6 days and finally inoculated (7% inoculum) into 100 ml of V6 liquid medium (see Example 1). After 6 days of growth at 28° C. and 200 rpm, the mycelium was harvested by centrifugation and washed three times by sterile saline solution, then diluted to provide a suitable inoculum. Aliquots of the suspension were streaked in a cross-hatched manner onto various media recommended by Shirling and Gottlieb (E. B. Shirling and D. Gottlieb, (1966): "Method for Characterization of *Streptomyces* species", Int. J. Syst. Bacteriol. 16: 313-340), and media recommended by S. A. Waksman (1961): "The Actinomycetes", The Williams and Wilkins Co., Baltimore. Vol. 2: 328-334).

The ability to use a variety of carbohydrates as a carbon and energy source was determined using medium ISP4 without starch, added with 1 ml/l of the vitamin solution described above as basal medium; each carbon source was added at the final concentration of 1% (w/v).

NaCl tolerance, pH range of growth as well as ability to grow at different temperatures was determined onto ISP2 medium. All media were incubated at 28° C. for three weeks; descriptions are referred to 21 days unless specified. Colour was assessed in natural daylight, using the Colour Atlas of Maerz and Paul (A. Maerz and M. R. Paul, 1950—A Dictionary of Colour, 2nd edition. McGraw-Hill Book Co. Inc., New York). Ability to reduce nitrates to nitrites was evaluated in sloppy Nitrate medium according to the procedure described by Williams et al. (S. T. Williams, M. Goodfellow, G. Alderson, E. M. H. Wellington, P. H. A. Sneath & M. J. Sackin, 1983—Numerical classification of *Streptomyces* and related genera—J. Gen. Microbiol. 129, 1743-1813).

Growth, colonial appearance, substrate and aerial mycelium colour and pigment production for strain *Microbispora* sp. ATCC PTA-5024 are recorded in Table I. Vegetative growth is present on most of the media used, differently from the aerial mycelium that is present only on some of them. No evident pigmentation is shown on any medium used. Physiological characteristics of the strain are presented in Table II. Growth and aerial mycelium production are present at 17° C. but not at 43° C. Production of aerial mycelium on ISP2 is present at pH higher than 6, while it is absent in presence of 1% NaCl.

The ability to use various carbohydrates for growth is shown in Table III.

TABLE I growth characteristics of *Microbispora* sp. ATCC PTA-5024

| MEDIUM | GROWTH & MORPHOLOGY | REVERSE COLOUR CODE |
|---|---|---|
| ISP 2 Yeast extract-Malt extract agar | Abundant growth, wrinkled surface; good production of pinkish (2A8) aerial mycelium. Slight production of orangish/light brown soluble pigment. | 5 E 12 orangish/red |
| ISP 3 Oatmeal agar | Abundant growth; good production of pinkish (2A8) aerial mycelium, particularly on the arms of the cross-hatched streakes. Slight production of orangish soluble pigment. | 11 H 10 orangish/pink |
| ISP 4 Inorganic salts-Starch agar | Good growth; no aerial mycelium produced. No soluble pigments produced. Starch hydrolysed. | 11 I 9 orange |
| Glu/Asp Glucose-Asparagine agar | Discrete growth, thin; production of thin, beige/pinkish (9B4) aerial mycelium on the arms of the cross-hatched streakes. No soluble pigments produced. | 12 K 12 orangish/light-brown |
| ISP 6 Peptone-yeast extract-iron agar | Scant growth, with pinkish single colonies grown in height, convolute, with a smooth surface; no aerial mycelium produced. No darkening of the medium. | nd |
| ISP 7 Tyrosine agar | Poor growth of a thin, orangish/light-brown substrate mycelium; no aerial mycelium produced. No darkening of the medium. | nd |
| ISP3 + YE Oatmeal/1% yeast extract agar | Abundant growth, wrinkled surface; very scant production of thin, pinkish aerial mycelium. No soluble pigments produced. | 4 B 12 orangish/red |

(ISP4 and Glucose-Asparagine Agar Added with 1 ml/L of Vitamins Solution)

TABLE II physiological characteristics of *Microbispora* sp. ATCC PTA-5024.

| TEST | REACTION |
|---|---|
| Starch hydrolysis | Positive |
| Casein hydrolysis | Negative |

TABLE II-continued physiological characteristics of *Microbispora* sp. ATCC PTA-5024.

| TEST | REACTION |
|---|---|
| Calcium malate digestion | Negative |
| Litmus milk peptonization | Negative |
| Litmus milk coagulation | Negative |
| Gelatin liquefaction | Negative to slightly positive |
| Tyrosine reaction | Negative |
| Nitrate reduction | Positive |
| PH range of growth (14 days) | no growth at 4.2, good at 5.5 to 8.8; not tested out of this range. Aerial mycelium absent at pH ≦ 6.5 |
| NaCl % tolerance | ≦2; absence of aerial mycelium at ≧1. |
| Temperature range of growth | 17° C. to 37° C. Presence of aerial mycelium in the whole range; no growth at 43° C. |

TABLE III utilization of carbon sources by *Microbispora* sp.

| Carbon source | Growth (14 days) |
|---|---|
| Arabinose | ++ |
| Cellulose | − |
| Fructose | ++ |
| Inositol | +/− |
| Mannitol | +++ |
| Raffinose | − |
| Rhamnose | − |
| Sucrose | +++ |
| Xylose | +++ |
| Glucose | ++ |
| Glycerol | ++ |
| No sugar | − |

+++ abundant;
++ good growth;
+ moderate growth;
+/− scant growth;
− no growth;
aerial mycelium always absent.

Chemotaxonomical Characteristics of *Microbispora* sp. ATCC PTA-5024

*Microbispora* sp. ATCC PTA-5024 was grown in GYM medium (glucose 4 g/l; yeast extract 4 g/l; malt extract 10 g/l) at 28° C. on a rotary shaker and the mycelium harvested, washed twice with sterile distilled water and subsequently freeze-dried. Analyses of amino acids were carried out according to the method of Staneck and Roberts, (J. L. Staneck and G. D. Roberts, (1974): "Simplified approach to identification of aerobic actinomycetes by thin-layer chromatography", Appl. Microbiol. 28: 226-231). Menaquinones and polar lipids were extracted following the procedure of Minnikin et al. (D. E. Minnikin, A. G. O'Donnell, M. Goodfellow, G. Alderson, M. Athalye, A. Schaal and J. H. Parlett, (1984): "An integrated procedure of isoprenoid quinones and polar lipids", J. Microbiol. Meth. 2: 233-241). Polar lipids were analysed by thin layer chromatography (D. E. Minnikin, V. Patel, L. Alshamaony, and M. Goodfellow, (1977): "Polar lipid composition in the classification of *Nocardia* and related bacteria", Int. J. Syst. Bacteriol. 27:104-117), menaquinones by HPLC (R. M. Kroppenstedt, (1982): "Separation of bacterial menaquinones by HPLC using reverse phase RP18 and a silver loaded ion exchanger as stationary phase", J. Liquid. Chromat. 5:2359-2367; R. M. Kroppenstedt, (1985): "Fatty acid and menaquinone analysis of actinomycetes and related organisms", in: Chemical Methods in Bacterial Systematics. No 20 SAB Technical Series pp. 173-199, M. Goodfellow and D. E. Minnikin eds, Academic Press, London) and fatty acid methyl esters by gas-liquid chromatography respectively (L. T. Miller, (1982): "A single derivatization method for bacterial fatty acid methyl esters including hydroxy acids", J. Clin. Microbiol. 16: 584-586; M. Sasser, (1990): "Identification of bacteria by gas chromatography of cellular fatty acids", USFCC News Letters 20:1-6). The presence of mycolic acids was checked by the method of Minnikin et al. (D. E. Minnikin, L. Alshamaony, and M. Goodfellow, (1975): "Differentiation of *Mycobacterium, Nocardia* and related taxa by thin layer chromatographic analysis of whole organism methanolyzates", J. Gen. Microbiol. 88: 200-204).

Whole cell hydrolyzates of strain *Microbispora* sp. ATCC PTA-5024 contain meso-diaminopimelic acid as the diammino acid of the peptidoglycan. The predominant menaquinones are MK-9(III, VIII-H$_4$), MK-9(H$_2$) and MK-9(H$_0$). The polar lipid pattern is characterized by the presence of phosphatidylethanolamine, methylphosphatidylethanolamine, phosphatidyl-glycerol, diphosphatidyl-glycerol, phosphatidyl-inositol, phosphatidyl-inositolmannosides and N-acetylglucosamine containing phospolipd, i.e. phospholipid type IV according to Lechevalier et al. (H. A. Lechevalier, C. De Briève and M. P. Lechevalier, (1977): "Chemotaxonomy of aerobic actinomycetes: phospholipid composition", Biochem. Syst. Ecol. 5: 246-260). The major components of fatty acid pattern are anteiso 15:0, iso 16:0, n-16:0, anteiso 17:0, and 10-methyl-heptadecanoic (10-Me-17:0), i.e 3c sensu Kroppenstedt (R. M. Kroppenstedt, (1985): "Fatty acid and menaquinone analysis of actinomycetes and related organisms", in: Chemical Methods in Bacterial Systematics. No 20 SAB Technical Series pp. 173-199. M. Goodfellow and D. E. Minnikin eds, Academic Press, London). Mycolic acids are not detected.

*Microbispora* sp. ATCC PTA-5024 16S rDNA Sequencing

The partial sequence of the 16 rRNA gene (16S rDNA), i.e 1443 nucleotides, corresponding to 95% of the entire rRNA, of strain *Microbispora* sp. ATCC PTA-5024, was achieved following published procedures (P. Mazza, P. Monciardini, L. Cavaletti, M. Sosio and S. Donadio, (2003): "Diversity of *Actinoplanes* and related genera isolated from an Italian soil", Microbial Ecol. 5:362-372). It is reported in SEQ ID NO 1.

This sequence was compared with that of strain *Microbispora corallina* NRRL 30420 (MF-BA-1768), as reported in U.S. Pat. No. 6,551,591 B1. The two sequences were aligned and differences were found at 31 out of 1456 aligned positions, accounting for an overall sequence divergence of 2.13%. Any two strains sharing less than 97.5% sequence identity usually belong to different species (Stackebrandt, E. and Embley, M. T. (2000) "Diversity of Uncultered Microorganisms in the Environment". In: *Nonculturable Microorganisms in the Environment*, R. R. Colwell and D. J. Grimes (eds). ASM, Press, Washington D.C., pp. 57-75). Therefore a 2% level of sequence divergence is quite high (Rosselló-Mora, R., and Amann, R. (2001). "The Species Concept for Prokaryotes". FEMS Microbiol. Rev. 25: 39-67)

and indicates that *Microbispora* sp. ATCC PTA-5024 and *Microbispora corallina* NRRL 30420 (MF-BA-1768) are different strains.

Identity of Strain *Microbispora* sp. ATCC PTA-5024

The strain producing antibiotic 107891 is assigned to the genus *Microbispora*, family Streptosporangiaceae because of the following chemotaxonomical and morphological characteristics:
 presence of meso-diaminopimelic acid in the cell wall;
 major amount of MK-9(III, VIII-H$_4$) and phospholipid type IV according to Lechevalier et al. (H. A. Lechevalier, C. De Briève and M. P. Lechevalier, (1977): "Chemotaxonomy of aerobic actinomycetes: phospholipid composition", Biochem. Syst. Ecol. 5: 246-260);
 fatty acid profile of 3c sensu Kroppenstedt (R. M. Kroppenstedt, (1992): "The genus *Nocardiopsis*", in: The Prokariotes, Vol II, pp. 1139-1156, A. Balows, H. Truper, M. Dworkin, W. Harder and K. H. Schleifer eds; New York, Springer-Verlag);
 absence of mycolic acids;
 formation of characteristic longitudinal pairs of spores on the tips of short sporophores laterally branching from aerial hyphae. Non-motile spores.
 partial sequence of the 16 rRNA gene (16S rDNA), i.e 1443 nucleotides, corresponding to 95% of the entire rRNA, reported in SEQ ID NO.1, showing >97% identity to 16S rDNA sequences from described *Microbispora* species.

As with other microorganisms, the characteristics of strain producing antibiotic 107891 are subject to variation. For example, artificial variants and mutants of the strain can be obtained by treatment with various known mutagens, such as U.V. rays, and chemicals such as nitrous acid, N-methyl-N'-nitro-N-nitrosoguanidine, and many others. All natural and artificial variants and mutants of strain *Microbispora* sp. ATCC PTA-5024 capable of producing antibiotic 107891 are deemed equivalent to it for the purpose of this invention and therefore within the scope of invention.

Extraction and Purification of Antibiotic 107891

As mentioned above, antibiotic 107891 is found almost equally distributed both in the mycelium and in the filtered fraction of the fermentation broth.

The harvested broth may be processed to separate the mycelium from the supernatant of the fermentation broth and the mycelium may be extracted with a water-miscible solvent to obtain a solution containing the 107891 antibiotic, after removal of the spent mycelium. This mycelium extract may then be processed separately or in pool with the supernatant according to the procedures reported hereafter for the supernatant fraction. When the water-miscible solvent may cause interferences with the operations for recovering the antibiotic from the mycelium extract, the water-miscible solvent may be removed by distillation or may be diluted with water to a non-interfering concentration.

The term "water-miscible solvent" as used in this application, is intended to have the meaning currently given in the art of this term and refers to solvents that, at the conditions of use, are miscible with water in a reasonably wide concentration range. Examples of water-miscible organic solvents that can be used in the extraction of the compounds of the invention are: lower alkanols, e.g. ($C_1$-$C_3$) alkanols such as methanol, ethanol, and propanol; phenyl ($C_1$-$C_3$) alkanols such as benzyl alcohol; lower ketones, e.g. ($C_3$-$C_4$) ketones such as acetone and ethyl methyl ketone; cyclic ethers such as dioxane and tetrahydrofuran; glycols and their products of partial etherification such as ethylene glycol, propylene glycol, and ethylene glycol monomethyl ether, lower amides such as dimethylformamide and diethylformamide; acetic acid dimethylsulfoxide and acetonitrile.

The recovery of the compound from the supernatant of the fermentation broth of the producing microorganism is conducted according to known per se techniques which include extraction with solvents, precipitation by adding non-solvents or by changing the pH of the solution, by partition chromatography, reverse phase partition chromatography, ion exchange chromatography, molecular exclusion chromatography and the like or a combination of two or more of said techniques. A procedure for recovering the compounds of the invention from the filtered fermentation broth includes extraction of antibiotic 107891 with water-immiscible organic solvents, followed by precipitation from the concentrated extracts, possibly by adding a precipitating agent.

Also in this case, the term "water-immiscible solvent" as used in this application, is intended to have the meaning currently given in the art to said term and refers to solvents that, at the conditions of use, are slightly miscible or practically immiscible with water in a reasonably wide concentration range, suitable for the intended use.

Examples of water-immiscible organic solvents that can be used in the extraction of the compounds of the invention from the fermentation broth are:

alkanols of at least four carbon atoms which may be linear, branched or cyclic such as n-butanol, 1-pentanol, 2-pentanol, 3-pentanol, 1-hexanol, 2-hexanol, 3-hexanol, 3,3-dimethyl-1-butanol, 4-methyl-1-pentanol, 3-methyl-1-pentanol, 2,2-dimethyl-3-pentanol, 2,4-dimethyl-3-pentanol, 4,4-dimethyl-2-pentanol, 5-methyl-2-hexanol, 1-heptanol, 2-heptanol, 5-methyl-1-hexanol, 2-ethyl-1-hexanol, 2-methyl-3-hexanol, 1-octanol, 2-octanol, cyclopentanol, 2-cyclopentylethanol, 3-cyclopenthyl-1-propanol, cyclohexanol, cycloheptanol, cyclooctanol, 2,3-dimethyl-cyclohexanol, 4-ethylcyclohexanol, cyclooctylmethanol, 6-methyl-5-hepten-2-ol, 1-nonanol, 2-nonanol, 1-decanol, 2-decanol, and 3-decanol; ketones of at least five carbon atoms such as methylisopropylketone, methylisobutylketone, methyl-n-amylketone, methylisoamylketone and mixtures thereof.

As known in the art, product extraction from the filtered fermentation broth may be improved by adjusting the pH at an appropriate value, and/or by adding a proper organic salt forming an ion pair with the antibiotic, which is soluble in the extraction solvent.

As known in the art, phase separation may be improved by salting the aqueous phase.

When, following an extraction, an organic phase is recovered containing a substantial amount of water, it may be convenient to azeotropically distill water from it. Generally, this requires adding a solvent capable of forming minimum azeotropic mixtures with water, followed by the addition of a precipitating agent to precipitate the desired product, if necessary. Representative examples of organic solvents capable of forming minimum azeotropic mixtures with water are: n-butanol, benzene, toluene, butyl ether, carbon tetrachloride, chloroform, cyclohexane, 2,5-dimethylfuran, hexane, and m-xylene; the preferred solvent being n-butanol.

Examples of precipitating agents are petroleum ether, lower alkyl ethers, such as ethyl ether, propyl ether, and butyl ether, and lower alkyl ketones such as acetone.

According to a preferred procedure for recovering antibiotic 107891, the filtered fermentation broth can be contacted with an adsorption matrix followed by elution with a polar, water-miscible solvent or a mixture thereof, concentration to an oily residue under reduced pressure, and precipitation with a precipitating agent of the type already mentioned above.

Examples of adsorption matrixes that can be conveniently used in the recovery of the compounds of the invention, are polystyrene or mixed polystyrene-divinylbenzene resins (e.g. M112 or S112, Dow Chemical Co.; Amberlite® XAD2 or XAD4, Rohm & Haas; Diaion HP 20, Mitsubishi), acrylic resins (e.g. XAD7 or XAD8, Rohm & Haas), polyamides such as polycaprolactames, nylons and cross-linked polyvinylpyrrolidones (e.g. Polyamide-CC 6, Polyamide-SC 6, Polyamide-CC 6.6, Polyamide-CC 6AC and Polyamide-SC 6AC, Macherey-Nagel & Co., Germany; PA 400, M. Woelm AG, Germany); and the polyvinylpirrolidone resin PVP-CL, (Aldrich Chemie GmbH & Co., KG, Germany) and controlled pore cross-linked dextrans (e.g. Sephadex® LH-20, Pharmacia Fine Chemicals, AB). Preferably, polystyrene resins are employed, particularly preferred being the Diaion HP 20 resin.

In the case of polystyrene resins, polystyrene-divinylbenzene resins, polyamide resins or acrylic resins a preferred eluent is a water-miscible solvent or its aqueous mixtures. The aqueous mixtures can contain buffers at appropriate pH value.

Also in this case, the term "water-miscible solvent", as used in this description and claims, is intended to have the meaning currently given in the art to said term as described above.

The successive procedures for the isolation and purification of the antibiotic may be carried out on the pooled extracts from the broth supernatant and from the mycelium. For example, when the portion of the antibiotic product contained in the filtered fermentation broth or supernatant is recovered by absorption on an absorption resin and the portion of the antibiotic product contained in the mycelium is extracted therefrom with a water-miscible solvent, followed by adsorption onto an absorption resin, the eluted fractions from each of the two sets of absorption resins may be combined, optionally after concentration, and then further processed as a unitary crop. Alternatively, when the two sets of absorption resins utilized for the separate extraction stages are of the same type and have the same functional characteristics, they may be pooled together and the mixture may be submitted to a unitary elution step, for instance, with a water-miscible solvent or a mixture thereof with water.

In any case, whatever may be the procedure adopted for recovering the crude antibiotic 107981, the successive purification step is usually carried out on the mixture of the crude materials resulting from the combination of the products originating from the separate extraction stages.

Purification of the crude antibiotic 107891, can be accomplished by any of the known per se techniques but is preferably conducted by means of chromatographic procedures. Examples of these chromatographic procedures are those reported in relation to the recovery step and include also chromatography on stationary phases such as silica gel, alumina, activated magnesium silicate an the like or reverse phase chromatography on silanized silica gel having various functional derivatizations, and eluting with water miscible solvents or aqueous mixture of water-miscible solvents of the kind mentioned above.

For instance, preparative HPLC chromatography may be employed, using RP-8 or RP-18 as stationary phase and a mixture of $HCOONH_4$ buffer: $CH_3CN$ as eluting system.

The active fractions recovered from the purification step are pooled together, concentrated under vacuum, precipitated by addition of a precipitating agent of the kind mentioned above and dried or lyophilised in single or iterative rounds. In the case the product contains residual amounts of ammonium formate or other buffering salts, these may be removed by absorption of the antibiotic 107891 on solid phase extraction column, for instance a reverse phase resin column such as SPE Superclean LCP18 Supelco (Bellefonte Pa., USA) followed by washing with distilled water and elution with an appropriate aqueous solvent mixture, e.g., ethanol:water. The antibiotic is then recovered by removing the elution solvents.

Accordingly, a purified antibiotic 107891 complex dried preparation is obtained as a white powder.

As usual in this art, the production as well as the recovery and purification steps may be monitored by a variety of analytical procedures including inhibitory assay against susceptible microorganisms and analytical control using the HPLC or HPLC coupled with mass spectrometry.

A preferred analytical HPLC technique is performed on a Waters instrument (Waters Chromathography, Milford, Mass.) equipped with a column Waters Simmetry-shield RP8, 5μ (250×4.6 mm) eluted at 1 ml/min flow rate and at 50° C. temperature.

Elution was with a multistep program: Time=0 (30% phase B); Time=8 min (30% Phase B); Time=28 min (40% of phase B).

Phase A was acetonitrile: 100 mM ammonium formate buffer (pH:5.0) 5:95 (v/v) and Phase B was acetonitrile. UV detector was at 282 nm.

The effluent from the column was splitted in a ratio 5:95 and the majority (ca. 950 μl/min) was diverted to photodiode array detector. The remaining 50 μl/min were diverted to the ESI interface of a Finnigan LCQ ion trap mass spectrometer (Thermoquest, Finnigan MAT, San Josè Calif.).

The mass spectrometric analysis was performed under the following conditions:

Sample Inlet Conditions:

Sheat gas ($N_2$) 60 psi;

Aux gas ($N_2$) 5 psi;

Capillary heater 250° C.;

Sample Inlet Voltage Settings:

Polarity both positive and negative;

Ion spray voltage +/−5 kV;

Capillary voltage +/−19V;

Scan conditions: Maximum ion time 200 ms;

Ion time 5 ms;

Full micro scan 3;

Segment: duration 30 min, scan events positive (150-2000 m/z) and negative (150-2000 m/z).

In these analytical HPLC conditions the antibiotic 107891 Factors A1 and A2 showed retention times of 13.2 min and 13.9 min, respectively. In the same HPLC system Ramoplanin A2 Factor (L. Gastaldo, R. Ciabatti, F. Assi, E. Restelli, J. K. Kettenring, L. F. Zerilli, G. Romanò, M. Denaro and B. Cavalleri, (1992): "Isolation, structure determination and biological activity of A-16686 Factors A'1, A'2 and A'3 glycolipodepsipeptide antibiotics", J. Ind. Microbiol. 11: 13-18) eluted with a retention time of 7.5 min.

Antibiotic 107891 Factors A1 e A2 may be separated from a purified sample of antibiotic 107891 complex by means of preparative HPLC.

Factor A1 was separated and purified on a Symmetry Prep. C18 column from the purified antibiotic 107891 complex dissolved in DMSO: formic acid 95:5 (v/v) using a 25 minutes linear gradient elution from 30% to 45% of phase B at 3.5 ml flow rate.

Phase B was acetonitrile. Phase A was 25 mM ammonium formate buffer pH 4.5: acetonitrile 95:5 (v/v). The eluted fractions containing pure antibiotic 107891 Factor A1 were pooled and concentrated under vacuum. The residual solution was lyophilised yielding pure Factor A1 as a white powder.

Factor A2 was separated and purified by isocratic elution on a Symmetry Prep. C18 column from a sample of purified antibiotic 107891 complex dissolved in acetic acid:acetonitrile: 100 mM ammonium formate buffer (pH 4) 50:120:80 (v/v) mixture. Isocratic elution was performed at a 7 ml flow rate with a mixture 100 mM ammonium formate buffer pH 4: acetonitrile in the proportion 82.5:17.5 (v/v). The eluted fractions containing pure antibiotic 107891 Factor A2 were pooled and concentrated under vacuum. The residual solution was liophilized yielding pure Factor A2 as a white powder.

Since antibiotic 107891 and its Factors A1 and A2, as shown by acid/base titration in 2-methoxyethanol (MCS): $H_2O$ 12:3 (v/v), contains a basic function, they are capable of forming salts with suitable acids according to conventional procedures and they may exist also in the free base form.

Antibiotic 107891 and its Factors A1 and A2, when obtained in the free base form, may be converted with acids into the corresponding salts, which include non-toxic pharmaceutically acceptable salts. Suitable salts include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and the like acids. The addition salts of antibiotic 107891 and its Factors A1 and A2, with acids can be prepared according to the usual procedures commonly employed. As an example, antibiotic 107891 or its Factor A1 or its Factor A2, in the free base form, is dissolved into the minimum amount of a suitable solvent, typically a lower alkanol, or a lower alkanol/water mixture, the stoichiometric amount of a suitable selected acid is gradually added to the obtained solution and the obtained salt is precipitated by the addition of a non-solvent. The addition salt which forms is then recovered by filtration or evaporation of the solvents.

Alternatively, these salts can be prepared in a substantially anhydrous form through lyophilization; in this case a salt of antibiotic 107891 or its Factor A1 or its Factor A2 with volatile acid is dissolved with a suitable amount of non-volatile acid. The solution is then filtered from any insolubles and is lyophilized in single or iterative rounds.

A specific addition salt may be also obtained from a solution of another salt form of antibiotic 107891 or its Factor A1 or its Factor A2 when the desired salt precipitates upon addition of the appropriate anion.

The transformation of the non salts compound of the invention into the corresponding addition salts, and the reverse, i.e. transformation of an addition salt of a compound of the invention into the non-salt form are within the ordinary technical skill and are encompassed by the present invention.

The formation of salts of antibiotic 107891 and its Factors A1 and A2 may serve several purposes, including the separation, purification of said antibiotic 107891 and its Factors A1 and A2 and their use as therapeutical agents or animal growth promoters. For therapeutical purposes, the pharmaceutically acceptable salts are usually employed.

The term "pharmaceutically acceptable salts" identifies those non-toxic salts which can be utilized in the therapy of warm-blooded animals.

The antibiotic 107981 complex, its Factors A1 and A2 and a mixture of said Factors in any proportion can be administered as such or in mixtures with pharmaceutically acceptable carriers and can also be administered in conjunction with other antimicrobial agents such as penicillins, cephalosporins, aminoglycosides and glycopeptides.

Conjunctive therapy, thus includes sequential, simultaneous and separate administration of the active compound in a way that the therapeutic effects of the first administered one is not entirely disappeared when the subsequent is administered.

The compounds of the invention, or its pharmaceutically acceptable addition salts, can be formulated into forms suitable for parenteral, oral or topical administration. For iv. administration in the treatment of any infection involving a microorganism susceptible to the antibiotic, a parenteral formulation is, for instance, in water with an appropriate solubilising agent such as polypropylene glycol or dimethylacetamide and a surface-active agent (e.g. polyoxyethylene sorbitan mono-oleate or polyethoxylated castor oil) or cyclodextrins or phospholipid based formulations in sterile water for injection. An injectable formulation may be also obtained with an appropriate cyclodextrin.

The antibiotic 107981 complex, its Factors A1 and A2 and a mixture of said Factors in any proportion may also be used in a suitable pharmaceutical form such as a capsule, a tablet or an aqueous suspension for oral administration or with conventional creams or jellies for topical applications. Besides their use as medicaments in human and veterinary therapy, the compounds of the invention can also be used as animal growth promoters. For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration. Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., S. Francisco, U.S.A., 1969 or "Livestock Feeds and Feeding" 0 and B books, Corvallis, Ore., U.S.A., 1977).

Physico-Chemical Characteristics of Antibiotic 107891

A) Mass Spectrometry: in MS experiments on a Thermofinnigan LCQ deca instrument fitted with an electrospray source, using Thermofinnigan calibration mix, antibiotic 107891 gives two doubly protonated ions at m/z=1124 and at m/z 1116 corresponding to lowest isotope composition of the complex Factors A1 and A2, respectively. The electrospray conditions were: Spray Voltage: 4.7 kV; Capillary temperature: 220° C.; Capillary Voltage: 3 V; Infusion mode 10 µl/min. Spectra were recorded from a 0.2 mg/ml solution in methanol/water 80/20 (v/v) with trifluoroacetic acid 0.1% and are reported in FIG. 1A (full scan low resolution spectrum) and 1B (zoom-scan high resolution spectrum).

B) The infrared spectrum of antibiotic 107891 recorded in KBr with a Bruker FT-IR spectophotometer model IFS 48, exhibits absorption maxima at ($cm^{-1}$): 3263; 2929; 1661; 1533; 1402; 1114; 1026. Infrared spectrum is reported in FIG. 2. Absorption bands at 1631, 1596 and 1346 are attributed to residual amounts of ammonium formate.

C) The U.V. spectrum of antibiotic 107891, performed in methanol/$H_2O$ (in ratio 80:20) with a Perkin-Elmer spectrophotometer Lambda 16, exhibits two shoulders at 226 and 267 nm. UV spectrum is reported in FIG. 3

D) $^1$H-NMR spectrum was recorded in the mixture methanol-d4:$H_2O$ (pH 4.3 HCl) 40:10 (v/v) at 40° C. on a Bruker AMX 600 spectrometer applying a water suppression sequence. As internal standard the residual signal of methanol-d4 at 3.31 ppm was considered.

The $^1$H-NMR spectrum of antibiotic 107891 is reported in FIG. 4. $^1$H NMR spectrum of antibiotic 107891 dissolved in methanol-d4:$H_2O$ (0.01N HCl) 40:10 (v/v) exhibits the following groups of signals (in ppm) at 600 MHz using MeOH-d4 as internal standard (3.31 ppm), [δ=ppm, multiplicity; (attribution)]: 0.93 d ($CH_3$), 0.98 d ($CH_3$), 1.07 t (overlapped $CH_3$'s), 1.18 t (overlapped $CH_3$'s), 1.26 s ($CH_3$), 1.30 t (overlapped $CH_3$'s), 1.62-1.74 m ($CH_2$), 1.78 d ($CH_3$), 1.80 d ($CH_3$), 2.03 m ($CH_2$), 2.24 m (CH), 2.36 m ($CH_2$), 2.72-3.8 m (peptidic alpha CH's), 3.8-5.2 m (peptidic alpha CH's), 5.53-6.08 s ($CH_2$), 5.62 d (CH double bond), 6.42 m (CH), 6.92 d (CH double bond), 7.0-7.55 m (aromatic CH's), 7.62-10.4 d and m (aromatic and peptidic NH's).

E) $^{13}$C-NMR spectrum was recorded in the mixture methanol-d4:$H_2O$ (pH 4.3 HCl) 40:10 (v/v) at 40° C. on a Bruker AMX 600 spectrometer using as internal standard the residual signal of methanol-d4 at 49.15 ppm. The $^{13}$C-NMR spectrum bb decoupled of antibiotic 107891 is reported in FIG. 5.

$^{13}$C NMR spectrum of antibiotic 107891 dissolved in methanol-d4:$H_2O$ (0.01 N HCl) 40:10 (v/v) exhibits the following groups of signals (in ppm) at 600 MHz using MeOH-d4 as internal standard (49.15 ppm), [δ=ppm; (attribution)]: 13.6-23.2 (aliphatic $CH_3$'s), 26.16-73 (aliphatic $CH_2$'s and peptidic alpha CH's), 105-136 (aromatic and double bonds CH's and quaternary carbons), 164.3-176.3 (peptidic carbonyls).

F) Antibiotic 107891 complex was dissolved in 2-methoxyethanol (MCS):$H_2O$ 12:3 (v/v) containing a molar excess of 0.01 M hydrochloric acid. The solution was then back titrated with a solution of 0.01 N potassium hydroxide. The resulting titration curve showed one basic ionizable function.

Amino Acids Composition of Antibiotic 107891 and its Factors A1 and A2

A) Determination of "Acid Resistant" Aminoacids in Antibiotic 107891 Complex

Antibiotic 107891 was submitted to complete acidic hydrolysis (HCl 6N, 105° C., 24 h) and amino acid components of the antibiotic resistant to acid treatment were identified. Acid labile amino acids are not detectable with this approach. The hydrolysate was studied by HPLC-MS and GC-MS analysis, after suitable derivatization, in comparison with a mixture of standard amino acids similarly derivatized. For HPLC analysis the hydrolyzed sample was treated with 6-aminoquinolyl-N-hydroxysuccinimidyl carbamate (AccQ-Tag™ Fluor reagent kit), for GC anlysis with a mixture of 3N HCl in anhydrous methanol and trifluoroacetic anhydride.

The qualitative HPLC analysis was carried out on a liquid chromatography system with simultaneous DAD and MS detection. The HPLC method had the following conditions:

Column: AccQ-Tag™ (Waters C18 NovoPak 4 µm 3.9×150 mm)

Column temperature: 37° C.

Flow: 1 mL/min.

Phase A: Ammonium acetate 140 mM pH 5 (acetic acid)

Phase B: Water:acetonitrile 60:40 (v/v)

Elution Program

| | Time (min.) | | | | |
|---|---|---|---|---|---|
| | 0 | 5 | 30 | 35 | 40 | 41 |
| % B | 5 | 5 | 80 | 95 | 95 | 5 |

UV detection: 254 nm

MS conditions were the following:

Spectrometer: Finnigan LCQ Deca equipped with standard electrospray source.

Capillary temperature: 250° C.

Source voltage: 4.70 KV

Source current: 80 µA

Capillary voltage: −15V

The qualitative GC analysis was carried out on a gas cromatographer fitted with MS-EI detection.

The GC method had the following conditions:

Column: J & W Scientific DB-5, 30 m×0.254 mm ID×0.25 µm FT

Carrier gas: helium

Injection mode: splitless

Injector temperature: 200° C.

Transfer line temperature: 300° C.

Temperature program: from 50° C. to 100° C. at 2.5° C./min (10 min), from 100° C. to 250° C. at 10° C./min (15 min), 15 min at 250° C.

Injection volume: 1 μl

MS conditions were the following:

Spectrometr: Finnigan TSQ700

Ionisation mode: Electron impact

Voltage Setting:

Filament current: 400 mA

Electron multiplier: 1400 V

Electron energy: 70 eV

Positive Ion Mode

Scan Condition:

Scan range: 40-650 amu

Scan time: 1 sec

In the LC/MS and GC/MS chromatograms obtained on the hydrolysate of antibiotic 107891, the following amino acids were identified along with other unidentified peaks: lanthionine, methyllanthionine, glycine, proline, valine, aspartic acid (NMR studies indicate that this is a transformation product of asparagine, which generates aspartic acid by hydrolysis), phenylalanine and leucine.

Antibiotic 107891 Factors A1 and A2 were submitted to complete acidic hydrolysis in the same conditions (derivatization and HPLC-MS) reported for the complex. The GC-MS analysis was carried out on a Thermo Finnigan Trace GC-MS instrument equipped with PTV injector The GC method had the following conditions:

Column: Restek RTX-5MS, 15 m×0.25 mm ID×0.25 μm FT

Carrier gas: helium

Interface temperature: 250° C.

Temperature program: 1.5 min at 50° C., from 50° C. to 100° C. at 20° C./min, 1 min at 100° C., from 100° C. to 135° C. at 20° C./min, 1 min at 135° C., from 135° C. to 250° at 20° C./min, 1 min at 250° C.

Injection volume: 1 μl

Injector: splitless mode, base temperature 50° C., transfer temperature 280° C., transfer rate 14.5° C./min MS conditions were the following:

Ionisation mode: Electron impact

Voltage Setting:

Filament current: 149 μA

Electron multiplier: 200 V

Electron energy: 70 eV

Positive Ion Mode:

Scan Condition:

Scan range: 33-500 amu

Scan time: 0.6 sec

In the hydrolysate of Factor A1 of antibiotic 107891, HPLC/MS and GC/MS chromatograms showed the presence of the following amino acids along with other unidentified peaks: lanthionine, methyllanthionine, glycine, proline, valine, aspartic acid (NMR studies indicate that this is a transformation product of asparagine, which generates aspartic acid by hydrolysis), phenylalanine and leucine.

The above procedure carried out on Factor A2 revealed the presence of the following amino acids along with other unidentified peaks: lanthionine, methyllanthionine, glycine, proline, valine, aspartic acid (NMR studies indicate that this is a transformation product of asparagine, which generates aspartic acid by hydrolysis), phenylalanine and leucine.

B) Determination of 5-Chlorotyptophan in Antibiotic 107891 Complex and in its Factor A1 and Factor A2.

Complete hydrolysis of purified 107891 complex and its single Factors A1 and A2 was performed according to the method described by Simpson R J, Neuberger M R, Liu T Y, "Complete Aminoacid Analysis of Proteins from a Single Hydrolysate". Journal Biol. Chem (United States), Apr. 10, 1976, 251 (7), 1936-40.

This hydrolysis procedure prevents degradation of amino acids normally unstable during mineral acid digestion and thus allows the determination of these amino acids, including tryptophan, from a hydrolysate of a peptide. A standard sample of 5-chloro-DL-tryptophan was purchased from Biosynt AG, Staad, Switzerland and its structure was confirmed by NMR analysis; DL-tryptophan was purchased from Merck KGaA, Darmstadt, Germany.

Factor A1 (1.5 mg) was suspended in 0.6 ml of 4N methanesulfonic acid containing 0.2% (w/v) 3-(2-aminoethyl)indole as catalyst for the hydrolysis. The hydrolysis was carried out at 115° C. for 16 hours. The hydrolysate was then neutralized with 5N NaOH and diluted with an equal amount of distilled water. 100 μl of this solution was analysed by LC-MS. The separation was performed on a Symmetry $C_{18}$ (5 μm) 4.6×250 mm. column (Waters Co. Milford Mass., USA) equipped with a Symmetry $C_{18}$ (5 μm) 3.9×20 mm precolumn. Elution was performed at 1 ml/min flow rate with a 25 min. linear gradient from 0% to 50% of Phase B. Phase A was 25 mM $HCOONH_4$ buffer pH 4.5:$CH_3CN$ 95:5 (v/v) and Phase B was $CH_3CN$. UV detection was at 280 nm. The HPLC equipment was coupled with a Finnigan LCQ ion trap Mass Spectrometer (Thermoquest, Finnigan MAT, San Josè, CA, USA). 50 μl/min of the effluents from the column were diverted to the Electrospray Ionization (ESI) interface of the LCQ mass spectrometer. The MS analysis was performed under the following conditions: sample inlet: shear gas ($N_2$) 60 psi; capillary heater 210° C.; sample inlet voltage polarity: both positive and negative; ion spray voltage +/−4.5 KV; capillary voltage +/−21 V; scan conditions: maximum ion time 50 ms; full micro: scan 3.

Standards of tryptophan and 5-chlorotryptophan eluted at retention times of 8.1 minutes and 11.5 minutes corresponding to a $M+H^+$ at m/z 205 and 239, respectively. In the hydrolysate of antibiotic 107891 Factor A1 the presence of a peak at 11.5 minutes with m/z at 238.97 indicated the presence of 5-chlorotryptophan.

Standard tryptophan was detectable with the chromatographic system used with a detection limit of 0.3 μg/ml. This value is lower than the value which would have been indicative of the presence of said aminoacid in the tested antibiotic sample. No tryptophan was detected within the above said limit in the chromatogram of the hydrolysate of antibiotic 107891 Factor A1. Identical results were obtained from LC-MS analysis of a hydrolysate of Factor A2 and of a hydrolysate of a purified sample of antibiotic 107891 complex.

Mass Spectrometry of Antibiotc 107891 Factor A1 and Factor A2

Antibiotic 107891 Factor A1 gives a doubly protonated ion at m/z=1124 and Factor A2 at m/z 1116 corresponding to the lowest isotope composition in MS experiments on a Thermofinnigan LCQ deca instrument fitted with an electrospray source, using Thermofinnigan calibration mix. The electrospray conditions were: Spray Voltage: 4.7 kV; Capillary temperature: 250° C.; Capillary Voltage: 8 V; Infusion mode 10 µl/min. Spectra were recorded from a 0.1 mg/ml solution in acetonitrile:water 50:50 (v/v) with acetic acid 0.5% and are reported in FIG. 6A (full scan low resolution spectrum) and 6B (zoom-scan high resolution spectrum) and in FIG. 7A (full scan low resolution spectrum) and B (zoom-scan high resolution spectrum).

The exact mass of antibiotic Factor A1 and Factor A2 has been determined by using a Bruker Daltonics APEX II, 4.7 Tesla spectrometer fitted with an electrospray source. On the basis of these data, Factor A1 is assigned a molecular weight of 2246.71±0.06, calculated monoisotopic mass from $[M+2H]^{2+}$ at m/z 1124.36124 (accuracy 30 ppm), determined by high resolution ESI-FTMS. Factor A2 is assigned a molecular weight of 2230.71±0.06, calculated monoisotopic mass from $[M+2H]^{2+}$ at m/z 1116.36260 (accuracy 30 ppm), determined by high resolution ESI-FTMS.

Comparison of Antibiotic 107891 Factor A1 and Factor A2 with Antibiotics MF-BA-1768$\alpha_1$ and MF-BA-1768$\beta_1$ A) *Microbispora corallina* NNRL 30420 (MF-BA-1768), described in U.S. Pat. No. 6,551,591 B1, was acquired from NNRL collection. In an exploratory experiment, the *M. corallina* NNRL 30420 (MF-BA-1768) strain has been fermented in Erlenmeyer flask in the conditions described in U.S. Pat. No. 6,551,591 B1. The harvested broth was extracted by dilution with methanol. After centrifugation of the mycelium, the supernatant was loaded on a HP20 polystyrenic absorption resin, eluted with a methanol:water 70:30 mixture, which was reduced to small volume and was then lyophilized.

In the chromatogram two peaks showed 1091 and 1108 $[M+2H]^{2+}$ signals, corresponding to the $[M+2H]^{2+}$ reported in U.S. Pat. No. 6,551,581 B1 for MF-BA-1768$\beta_1$ and MF-BA-1768$\alpha_1$, respectively. The above extract was then spiked with antibiotics 107891 Factors A1 and A2 and the mixture was analyzed by LC-MS. The peaks of antibiotics MF-BA-1768$\beta$1 and MF-BA-1768$\alpha$1 and of antibiotics 107891 Factors A1 and A2 were found to have distinct retention time and distinct $[M+2H]^{2+}$ MS fragments.

B) In a further experiment, a 30 l thank fermentation of *Microbispora* sp. strain NRRL 30420 (MF-BA-1768) was performed and the harvested broth was processed by following the description of U.S. Pat. No. 6,551,591 B1. After purification steps sequentially on HP20 polystyrenic resin and polyamide CC 6 0.1-0.3 mm (Macherey-Nagel) resin, two individual substances were obtained in pure form by preparative HPLC on a µ10 particle size C18 Phenomenex (Torrance Calif., USA) Luna (250×12.2 mm) column eluted at flow rate 27 ml/min with the following multistep program: Time=0 min (32% of phase B); Time=8 min (32% of phase B); Time=20 min (36% of phase B); Time=32 min (90% Phase B). Phase A was formic acid 0.05% (v/v) in water, Phase B was $CH_3CN$.

These substances showed antibacterial activity against staphylococci and enterococci as shown in Table IV. In LC-MS experiments the two substances showed $[M+2H]^{++}$ double protonated ions signals corresponding to antibiotic MF-BA-1768$\alpha$1 and MF-BA-1768$\beta$1, as described in U.S. Pat. No. 6,551,591 B1.

TABLE IV

| | MIC (µg/ml) | | | | |
| --- | --- | --- | --- | --- | --- |
| STRAIN | MF-BA-1768$\alpha$1 | MF-BA-1768$\beta$1 | 107891 A1 | 107891 A2 | 107891 complex |
| 1400 *Staphylococcus aureus* cl. isol. Met r | 0.13 | 0.5 | 0.13 | 0.13 | 0.13 |
| 568 *Enterococcus faecium* cl. isol. | 4 | 16 | 1 | 2 | 2 |
| 569 *Enterococcus faecium* cl. isol. Van A | 4 | 8 | 1 | 2 | 2 |
| 559 *Enterococcus faecalis* cl. isol. | 4 | 8 | 1 | 2 | 1 |
| 560 *Enterococcus faecalis* cl. isol. Van A | 4 | 8 | 0.5 | 1 | 0.5 |

Experimental conditions of the antimicrobial tests were the same as those utilized for the tests reported in Table VI below.

The LC-MS analyses of the isolated antibiotics MF-BA-1768$\alpha_1$ and MF-BA-1768$\beta_1$ were performed on a Symmetry $C_{18}$ (5:m) 4.6×250 mm. column (Waters; Milford Mass., USA) equipped with a Symmetry $C_{18}$ (5:m) 3.9×20 mm precolumn (both maintained in an oven at 50° C. temperature). Elution was performed at 1 ml/min flow rate with the following multistep elution program: Time=0 min (30% Phase B); Time=8 min (30% Phase B); Time=20 min (45% Phase B); Time=24 min (90% Phase B); and Time=28 min (90% Phase B). Phase A was 25 mM $HCOONH_4$ buffer pH 4.5:$CH_3CN$ 95:5 (v/v) and phase B was $CH_3CN$. The HPLC equipment was coupled with a Finnigan LCQ ion trap Mass Spectrometer (Thermoquest, Finnigan MAT, San Josè Calif., USA). 100 µl/min of the effluents from the column were diverted to the ESI interface of the LCQ Mass Spectrometer.

The MS analysis was performed under the following conditions: sample inlet: sheat gas flow (N$_2$) 25 psi, aux gas flow 5 psi; capillary heater: 210° C.; sample inlet voltage polarity both positive and negative; ion spray voltage: +/−4.75 KV; capillary voltage: +/−12 V; scan conditions: maximum ion time 50 ms; full micro: scan 3.

Individual antibiotic Factors MF-BA-1768α$_1$ and MF-BA-1768β$_1$ and antibiotics 107891 Factors A1 and A2 were analyzed individually and in mixture. The results are summarized in the following Table V.

TABLE V

|  | Ret. time (min) | [M + 2H]$^{2+}$ |
| --- | --- | --- |
| MF-BA-1768β$_1$ | 12.86 | 1091 |
| Antibiotic 107891 A1 | 16.3 | 1124 |
| Antibiotic 107891 A2 | 16.81 | 1116 |
| MF-BA-1768α$_1$ | 18.1 | 1108 |

In the same chromatographic system ramoplanin factor A2 (L. Gastaldo, R. Ciabatti, F. Assi, E. Restelli, J. K. Kettenring, L. F. Zerilli, G. Romanò, M. Denaro and B. Cavalleri, (1992): "Isolation, structure determination and biological activity of A-16686 Factors A'1, A'2 and A'3 glycolipodepsipeptide antibiotics", J. Ind. Microbiol. 11: 13-18) was eluted with 11.00 min retention time.

NMR Spectroscopy of Antibiotic 107891 Factor A1 and Factor A2

$^1$H-NMR spectra of antibiotic 107891 Factor A1 and Factor A2 were recorded in the mixture CD$_3$CN:D$_2$O (1:1) at 298 K on a Bruker AMX 600 spectrometer applying a water suppression sequence. As internal standard the residual signal of acetonitrile-d3 at 1.94 ppm was considered.

A) The $^1$H-NMR spectrum of antibiotic 107891 Factor A1 is reported in FIG. 8.

$^1$H NMR spectrum of antibiotic 107891 Factor A1, dissolved in CD$_3$CN:D$_2$O (1:1), exhibits the following groups of signals (in ppm) at 600 MHz using CD$_3$CN as internal standard (1.94 ppm), [δ=ppm, multiplicity; (attribution)]: 0.84 d (CH$_3$), 0.89 d (CH$_3$), 0.94 t (overlapped CH$_3$'s), 1.1 d (CH$_3$), 1.13 d (CH$_3$), 1.15 t (overlapped CH$_3$'s), 149 m (CH$_2$), 1.69 d (CH$_3$), 1.75 m (CH$_2$), 2.11 m (CH), 2.26 m (CH), 2.5 m (CH$_2$), 2.68-3.8 m (peptidic CH$_β$'s), 3.8-5.0 m (peptidic CH$_α$'s), 5.45-6.17 s (CH$_2$), 5.58 d (CH double bond), 6.36 m (CH), 6.86 d (CH double bond), 7.0-7.45 m (aromatic CH's). The dimethyl sulfoxide signal is present at 2.58 ppm and the formate signal is also present at 8.33 ppm as impurities.

B) The $^1$H NMR spectrum bb decoupled of antibiotic 107891 Factor A2 is reported in FIG. 9.

$^1$H NMR spectrum of antibiotic 107891 Factor A2, dissolved in CD$_3$CN:D$_2$O (1:1), exhibits the following groups of signals (in ppm) at 600 MHz using CD$_3$CN as internal standard (1.94 ppm), [δ=ppm, multiplicity; (attribution)]: 0.84 d (CH$_3$), 0.88 d (CH$_3$), 0.94 d (CH$_3$), 1.06 d (CH$_3$), 1.14 d (CH$_3$), 148 m (CH$_2$), 1.65-1.75 m (CH$_2$), 1.67 d (CH$_3$), 2.15 m (CH), 2.25 m (CH), 2.5 m (CH$_2$), 2.77-3.8 m (peptidic CH$_β$'s), 3.8-4.9 m (peptidic CH$_α$'s) 5.45-6.14 s (CH$_2$), 5.59 d (CH double bond), 6.34 m (CH), 6.84 d (CH double bond), 7.0-7.42 m (aromatic CH's). The dimethyl sulfoxide signal is present at 2.58 ppm and the formate signal is also present at 8.32 ppm as impurities.

$^{13}$C-NMR spectra of antibiotic 107891 Factor A1 and Factor A2 were recorded in the mixture CD$_3$CN:D$_2$O (1:1) at 298 K on a Bruker AMX 600 spectrometer using as internal standard the residual signal of acetonotrile-d3 at 1.39 ppm.

C) The $^{13}$C-NMR spectrum of antibiotic 107891 Factor A1 is shown in FIG. 10. $^{13}$C NMR spectrum of antibiotic 107891 Factor A1, dissolved in CD$_3$CN:D$_2$O (1:1), exhibits the following groups of signals (in ppm) at 600 MHz using CD$_3$CN as internal standard (1.39 ppm), [δ=ppm; (attribution)]: 13.6-23.03 (aliphatic CH$_3$'s), 25.69-77.9 (aliphatic CH$_2$'s and peptidic CH$_α$'s), 105-137.3 (aromatic and double bonds CH's and quaternary carbons), 165.6-176.6 (peptidic carbonyls).

D) The $^{13}$C-NMR spectrum bb decoupled of antibiotic 107891 Factor A2 is shown in FIG. 11.

$^{13}$C-NMR spectrum of antibiotic 107891 Factor A2, dissolved in CD$_3$CN:D$_2$O (1:1), exhibits the following groups of signals (in ppm) at 600 MHz using CD$_3$CN as internal standard (1.39 ppm), [δ=ppm; (attribution)]: 13.6-22.9 (aliphatic CH$_3$'s), 25.65-73 (aliphatic CH$_2$'s and peptidic CH$_α$'s), 105-137.3 (aromatic and double bonds CH's and quaternary carbons), 165.7-176.1 (peptidic carbonyls).

UV and I.R. Spectra of Antibiotic 107891 Factor A1 and Factor A2.

A) The infrared spectrum of antibiotic 107891 Factor A1 recorded in KBr with a Bruker FT-IR spectophotometer model IFS 48, exhibits absorption maxima at (cm$^{-1}$): 3294; 3059; 2926; 1661; 1529; 1433; 1407; 1287; 1114; 1021. Infrared spectrum is reported in FIG. 12.

B) The U.V. spectrum of antibiotic 107891 Factor A1 recorded in methanol:H$_2$O 80:20 (v/v) with a Perkin-Elmer spectrophotometer Lambda 16, exhibits two shoulders at 226 and 267 nm. U.V. spectrum is reported in FIG. 13.

C) The infrared spectrum of antibiotic 107891 Factor A2 recorded in KBr with a Bruker FT-IR spectophotometer model IFS 48, exhibits absorption maxima at (cm$^{-1}$): 3296; 3060; 2928; 1661; 1529; 1433; 1407; 1288; 1116. Infrared spectrum is reported in FIG. 14.

D) The U.V. spectrum of antibiotic 107891 Factor A2 recorded in methanol:H$_2$O 80:20 (v/v) with a Perkin-Elmer spectrophotometer Lambda 16, exhibits two shoulders at 226 and 267 nm. U.V. spectrum is reported in FIG. 15.

On the basis of the physico chemical data reported above, the following structure formula can be assigned to antibiotic 107891:

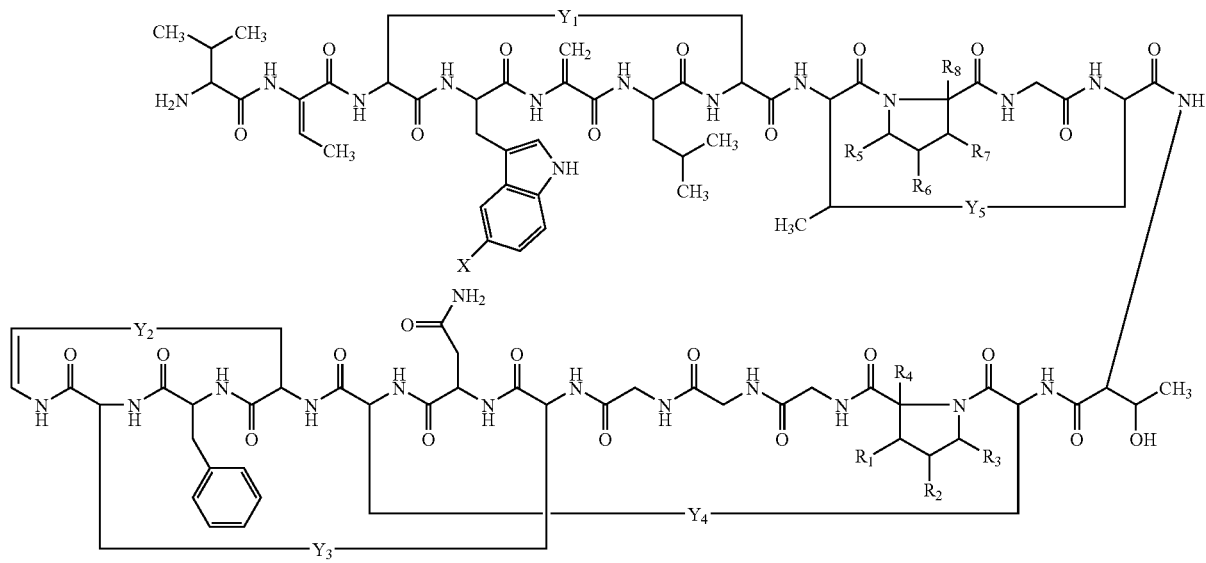

wherein X is H or a halogen (F, Cl, Br, I), $Y_1$, $Y_2$, $Y_3$, $Y_4$, and $Y_5$ may independently be S, S—O$^{31}$, S=O, O$^{31}$ 13 S=O, and O=S=O, and wherein $R_1$, $R_2$, $R_3$, $R_4$, $R_5$, $R_6$, $R_7$, and $R_8$ may independently be H, OH, alkyl (branched or unbranched, substituted or unsubstituted), or aryl (substituted or unsubstituted).

In an alternative embodiment, $R_1$, $R_2$, $R_3$, and $R_4$ may be H or OH. Therefore, the possible combinations of $R_1$, $R_2$, $R_3$, and $R_4$ include the following.

| $R_1$ | $R_2$ | $R_3$ | $R_4$ |
|---|---|---|---|
| H | H | H | H |
| OH | H | H | H |
| H | OH | H | H |
| H | H | OH | H |
| H | H | H | OH |
| OH | OH | H | H |
| OH | H | OH | H |
| OH | H | H | OH |
| H | OH | OH | H |
| H | H | OH | OH |
| H | OH | H | OH |
| OH | OH | OH | H |
| OH | OH | H | OH |
| OH | H | OH | OH |
| H | OH | OH | OH |
| OH | OH | OH | OH |

Similarly, $R_5$, $R_6$, $R_7$, and $R_8$ may be H or OH. Therefore, the possible combinations of $R_5$, $R_6$, $R_7$, and $R_8$ include the following.

| $R_5$ | $R_6$ | $R_7$ | $R_8$ |
|---|---|---|---|
| H | H | H | H |
| OH | H | H | H |
| H | OH | H | H |
| H | H | OH | H |
| H | H | H | OH |
| OH | OH | H | H |
| OH | H | OH | H |
| OH | H | H | OH |
| H | OH | OH | H |
| H | H | OH | OH |
| H | OH | H | OH |
| OH | OH | OH | H |
| OH | OH | H | OH |
| OH | H | OH | OH |
| H | OH | OH | OH |
| OH | OH | OH | OH |

Moreover, on the basis of the physico chemical data reported above, the following structure formula can be assigned to antibiotic 107891 Factor A1, wherein X is Cl; $Y_1$, $Y_2$, $Y_3$, $Y_4$, and $Y_5$ are S; $R_1$ is H; $R_2$ is OH; $R_3$ is H; and $R_4$, $R_5$, $R_6$, $R_7$, and $R_8$ are H, which is a preferred embodiment of the invention together with the pharmaceutically acceptable salts thereof:

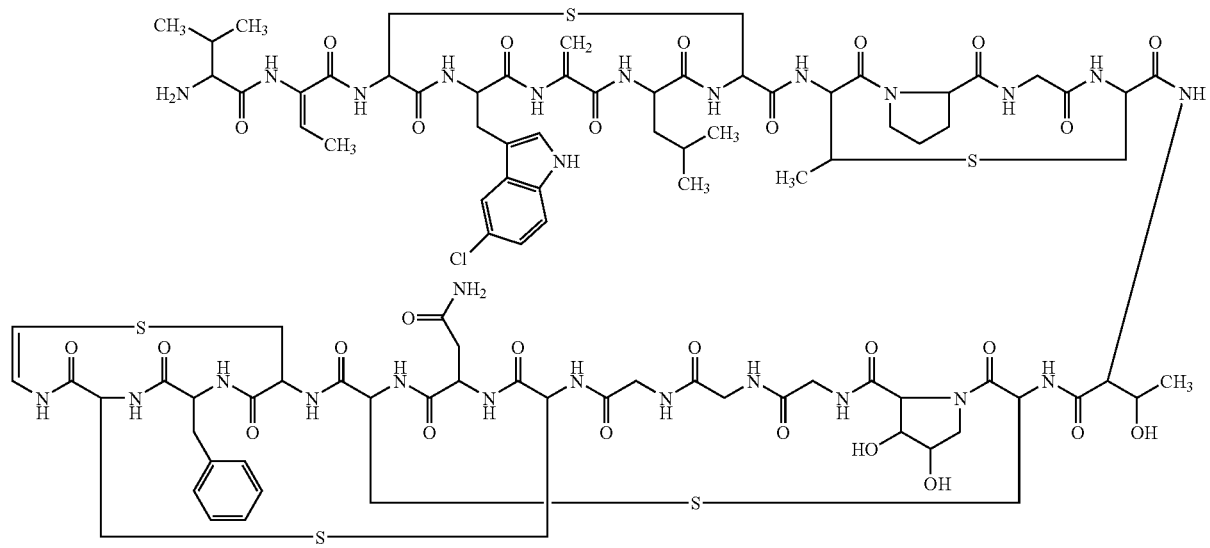

Additionally, on the basis of the physico chemical data reported above, the following structure formula can be assigned to antibiotic 107891 Factor A2, wherein X is Cl; $Y_1$, $Y_2$, $Y_3$, $Y_4$, and $Y_5$ are S; $R_1$ is OH; $R_2$ is OH; $R_3$ is H; and $R_4$, $R_5$, $R_6$, $R_7$, and $R_8$ are H, which is a preferred embodiment of the invention together with the pharmaceutically acceptable salts thereof:

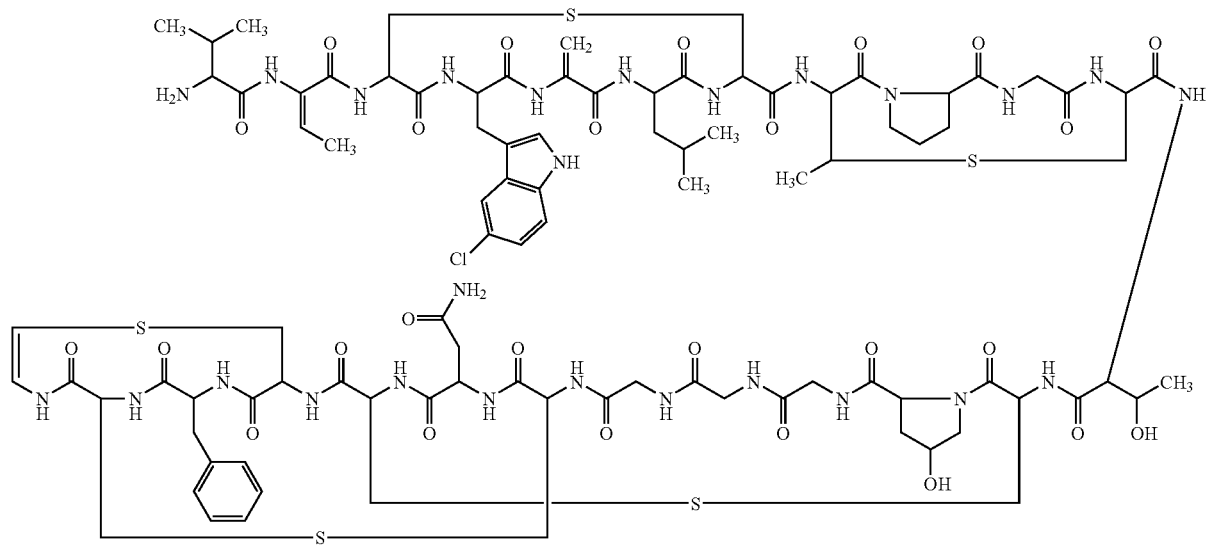

In Vitro Biological Activity of Antibiotic 107891

Antimicrobial activity of the antibiotic 107891 was determined by the broth microdilution method according to the National Committee for Clinical Laboratory Standards recommendations (NCCLS, document M7-A5).

The strains used were clinical isolates or strains from American Type Culture Collection (ATCC). The result of the tests are reported in Table VI and Table VII.

Antibiotic 107891 was dissolved in DMSO to obtain a 1000 μg/ml stock solution, and subsequently diluted in water to obtain working solution. The media used were cation-adjusted Mueller Hinton broth (CAMHB) for Staphylococci, M. catarrhalis, Enterococci and L. monocytogenes; Todd Hewitt broth (THB) for Streptococci; GC medium+1% Isovitalex+1% haemine for Neisseria spp.; Brain Hearth Infusion+1% C supplement for H. influenzae; Lactobacillus broth for Lactobacilli; Middlebrook 7H9 with Middlebrook OADC enrichment for M. smegmatis; RPMI 1640 Medium for C. albicans. Wilkins Chalgren broth+oxyrase (1:25 v/v) for Clostridia; Brucella broth containing cisteine (0.5 g/L) for Propionibacteria. Inocula for bacteria were $10^5$ CFU/ml. C. albicans inoculum was $1 \times 10^4$ CFU/ml. All the tests were performed in presence of 0.02% of bovine serum albumin (BSA). Cultures were incubated at 35° C. in air except Clostridia and Propioniobacteria strains that needed anaerobic atmosphere. After 18-24 hours visual readings were performed and MICs determined. The MIC was defined as the lower concentration of antibiotic at which there is no visible growth.

TABLE VI

Antimicrobial activity of antibiotic 107891

| Microorganism | | MIC (µg/ml) 107891 |
|---|---|---|
| 819 | Staph. aureus Smith ATCC1936 | ≦0.13 |
| 4061 | Staph. aureus LIM1 | ≦0.13 |
| 3798 | Staph. aureus clin. isolate VISA | 2 |
| 1400 | Staph. aureus clin. isolate Met-R | ≦0.13 |
| 613 | Staph. aureus clin. isolate Met-R | ≦0.13 |
| 3797 | Staph. aureus clin. isolate VISA Me | 2 |
| 4064 | Staph. aureus LIM2 CHSA Met-R | 0.5 |
| 1729 | Staph. haemolyticus Met-R | 8 |
| 1730 | Met-S | 2 |
| 147 | Staph. epidermidis ATCC12228 | ≦0.13 |
| 1139 | | 4 |
| 44 | Strept. pneumoniae Pen-S | ≦0.13 |
| 2858 | Pco-I | ≦0.13 |
| 49 | Strept. pyogenes | ≦0.13 |
| 559 | Ent. faecalis Van-S | 1 |
| 560 | Ent. faecalis Van-A | 0.5 |
| A533 | Ent. faecalis Van-A | 1 |
| 568 | Ent. faecium Van-S | 2 |
| 569 | Ent. faecium Van-A | 1 |
| B518 | Ent. faecium Van-A | 2 |
| A6345 | Ent. faecium Van-A Lnz-R | 4 |
| 3754 | Mycobacterium smegmatis | 32 |
| E34 | Listeria garvias | ≦0.13 |
| 148 | Listeria delbrueckii ATCC4797 | 4 |
| 1450 | Listeria monocytogenes | 0.125 |
| 833 | Haemophilus influenzae | 32 |
| 970 | Hasmophilus influenzae ATCC 19418 | 32 |
| 3924 | Moraxella catharralis | 1 |
| 16 | Moraxella catharralis ATCC8176 | 0.25 |
| 1613 | Neisseria meningitidis ATCC13090 | 0.5 |
| 997 | Neisseria gonorrhaee | 0.25 |
| 47 | Etcherichia coli | >128 |
| 145 | Candida albicans | >128 |

TABLE VII

Antimicrobial activity of antibiotic 107891 against anaerobes bacteria

| Microorganism | MIC (µg/ml) Antibiotic 107891 |
|---|---|
| ATCC 27520 Propionibacterium limphophilum | 0.015 |
| ATCC 25564 Propionibacterium granulasum | 0.03 |
| ATCC 14157 Propionibacterium proptanicus | 4 |
| P9 Propionibacterium acnes | 0.125 |
| 1329 Propionibacterium acnes | 0.5 |
| ATCC 25746 Propionibacterium acnes | 0.015 |
| ATCC 6919 Propionibacterium acnes | 0.125 |
| ATCC 6922 Propionibacterium acnes | ≦0.0039 |
| ATCC 1348 Propionibacterium acnes | 0.25 |
| 4018 Clostridium difficile | ≦0.125 |
| 4025 Clostridium difficile | ≦0.125 |
| 4022 Clostridium difficile | ≦0.125 |
| 4032 Clostridium perfringens | ≦0.125 |
| 4043 Clostridium butyricum | ≦0.125 |
| 4009 Clostridium bestertuckii | ≦0.125 |
| 4052 Clostridium septicum | ≦0.125 |
| 60601 Peptostreptococcus anaerobius | >128 |

Antibiotic 107891 shows a good antibacterial activity against Gram-positive bacteria.

The MIC range against Staphylococcus spp., including Methicillin Resistant (MRSA) and Glycopeptides Intermediate (GISA) resistant strains, is =0.13-4 µg/ml and against recent clinical isolates of Enterococcus spp., including Vancomycin Resistant (VRE), is 0.5-4 µg/ml. Against Streptococcus spp. MICs are ≦0.13 µg/ml.

Antibiotic 107891 is also active against anaerobic Gram-positive strains; the MICs are ≦0.13 µg/ml against Clostridia and ≦0.004-4 µg/ml against Propionibacteria. Antimicrobial activities were showed against L. monocytogenes (MIC 0.125 µg/ml) and Lactobacilli strains (MICs range ≦0.13-4 µg/ml). Some Gram-negative bacteria are susceptible to antibiotic 107891; MICs are 1-0.25 µg/ml versus M. catharralis, 0.5-0.25 µg/ml against Neisseria spp. and 32 µg/ml against H. influenzae.

Antibiotic 107891 is not active against the E. coli and C. albicans strains tested.

In time-kill experiments antibiotic 107891 shows bactericidal activity against S. aureus GISA and E. faecalis VanA strain; at 24 hours the bactericidal concentration is the MIC value in Mueller Hinton broth.

S. aureus can cause life-threatening infections and MRSA is of particular clinical significance because it is resistant to all penicillins and cephalosporins and also to multiple other antibiotics; in addition it easily spreads from patient to patient causing outbreaks of infection with important implications for healthcare facilities (W. Witte, (1999): "Antibiotic resistance in Gram-positive bacteria: epidemiological aspects", Journal of Antimicrobial Chemotherapy 44:1-9). The Centers for Disease Control (CDC) National Nosocomial Infection Surveillance System (NNIS) reported that methicillin resistance among S. aureus in US hospitals increased from 2.4% in 1975 to 29% in 1991, with a higher degree of resistance in intensive care units (L. Archibald, L. Philips, D. Monnet, J. E. Jr Mc Gowan, F. Tenover, R. Gaynes, (1997): "Antimicrobial resistance in isolates from inpatients and outpatients in the United States: increasing importance of the intensive care unit", Clinic Infect. Dis. 24: 211-5). Nosocomial staphylococcal infections are associated with considerable morbidity and mortality, prolonging the duration of stay and increasing hospitalization costs. The majority of MRSA strains are resistant to several of the most commonly used antimicrobial agents, including macrolides, aminoglycosides, and the β-lactams antibiotics in current use, including the latest generation of cephalosporins.

Vancomycin resistant hospital-acquired pathogens responsible for infections (such as endocarditis, meningitis and septicemia) are posing an increasing therapeutic challenge (Y. Cetinkaya, P. Falk and C. G. Mayhall, (2000): "Vancomycin-resistant enterococci", Clin. Microbiol. Rev. 13: 686-707; L. B. Rice, (2001): "Emergence of vancomycin-resistant enterococci",. Emerg. Infec. Dis. 7:183-7).

S. pneumoniae and M. catarrhalis are recognized important pathogens of humans. They are a common cause of respiratory tract infections, particularly otitis media in children and lower respiratory tract infections in the eldery. M. catarrhalis and S. pneumoniae have been recently accepted as the commonest pathogens of the respiratory tract (M. C. Enright and H. McKenzy, (1997): "Moraxella (Branhamella) catarrhalis. Clinical and molecular aspect of a rediscovered pathogen", J. Med. Microbiol. 46:360-71).

Clostridia are responsible of different diseases: gas gangrene and related wound infections, tetanus, botulism, antibiotic associated diarrhea (CDAD) and pseumembranous colitis. Most of these microorganisms produce exotoxins that play an important role in the pathogenesis of the diseases. C. difficile is the causative agent responsible for 25% of cases of CDAD and for virtually all cases of pseudomembranous colitis. Over the last years the occurrence of C. difficile coinfection has occurred in patients with vancomycin resistant enteroccocal infection or colonization (J. G. Bartlett, (1992): "Antibiotic associated diarrhea", Clinic. Infect. Dis. 15: 573-581).

In Vitro Biological Activity of Antibiotic 107891 Factors A1 and A2

Table VIII reports the antimicrobial activities of the individual Factors A1 and A2 of antibiotic 107891. MICs were determined by microbroth dilution method as above described.

TABLE VIII

Antimicrobial activity of antibiotic 107891 Factors A1 and A2

| | | MIC ($\mu$g/ml) | |
|---|---|---|---|
| | Microorganism | Factor A1 | Factor A2 |
| 819 | Staph. aureus Met-S | ≦0.03 | ≦0.03 |
| 1524 | Staph. aureus Met-R | ≦0.03 | ≦0.03 |
| 2235 | Staph. aureus Met-R | 0.06 | 0.06 |
| 3894 | Staph. epidermidis Met-R | ≦0.03 | 0.06 |
| 3881 | Staph. epidermidis Met-R | 0.06 | ≦0.03 |
| 602 | Staph. haemolyticus Met-R | 0.25 | 0.25 |
| 3919 | Strept. pneumoniae Pen-R | ≦0.0015 | ≦0.0015 |
| 3915 | Strept. pneumoniae Pen-S | ≦0.0015 | ≦0.0015 |
| 4323 | Ent. faecalis VanA | ≦0.03 | ≦0.03 |
| J1 | Ent. faecalis VanA | 1 | 1 |
| 4341 | Ent. faecalis VanB | 0.5 | 0.5 |
| 4397 | Ent. faecalis VanB | 1 | 1 |
| 4341 | Ent. faecalis VanB | 2 | 2 |
| 6349 | Ent. faecium Van A LNZ-R | 2 | 2 |
| 4 | Ent. faecium Van A | 1 | 1 |
| 3 | Ent. faecium Van A | 0.5 | 0.5 |
| D561 | Ent. faecium Van A | 2 | 2 |
| A8 | Ent. faecium Van A | 0.5 | 0.5 |
| 4339 | Ent. faecium VanD | 0.25 | 0.25 |
| 4174 | Ent. gallinarum | 1 | 1 |
| 997 | Neisseria gonorrhaee | 0.5 | 0.25 |
| 1613 | Neisseria meningitidis | 0.25 | 0.25 |
| 1016 | Propionibacterium. acnes | <0.03 | 0.06 |

Biological Activity of Antibiotic 107891

Female ICR mice (Harlan Italia SpA—S. Pietro al Natisone, Italy) weighing 23-25 g were used in experiments of acute lethal infection in immunocompetent or neutropenic mice. Neutropenia was induced by two intraperitoneal administrations of cyclophosphamide, 200 and 100 mg/kg, at four days and one day, respectively, before the mice were infected.

Infection was induced by inoculating intraperitoneally in immunocompetent mice (8 animals/dose/treatment group) a bacterial suspension of either a clinical isolate of methicillin resistant staphylococcus (Staph. aureus SA3817) or a standard methicillin susceptible strain (Staph. aureus Smith ATCC19636), or by inoculating in neutropenic mice a clinical isolate of glycopeptide resistant enterococcus (Ent. faecalis A533). The bacterial challenges (ca $10^6$ cells/mouse) were given suspended in 0.5 mL of 5% bacteriological mucin (Difco). Untreated animals died within 24-72 h after infection. Antibiotic treatment began within 10-15 min after challenge. Antibiotic 107891 was administered once intravenously or subcutaneously in different aqueous formulations. The 50% effective dose ($ED_{50}$) and 95% confidence limits were calculated by the Spearman-Kärber method (D. J. Finney, (1952): "The Spearman-Kärber method", in: Statistical methods in biological assay. pp. 524-530, Charles Griffin & Co., Ltd., London) from the percentage of animals surviving at day 7. Results are reported in the following Table IX.

Antibiotic 107891 is not toxic up to the maximum tested dose of 200 mg/kg.

TABLE IX $ED_{50}$s of antibiotic 107891 in acute lethal infections in mice.

| Formulation | Strain | Route | $ED_{50}$ mg/kg | 95% confidence limits |
|---|---|---|---|---|
| A | MSSA | iv | 2.1 | 1.7-2.7 |
| | | sc | 2.1 | 1.7-2.7 |
| A | VanA | iv | 3.2 | 2.7-3.9 |
| | | sc | 11.1 | 9.2-13.5 |
| B | MRSA | sc | 4.2 | 3.5-5.1 |
| C | VanA | iv | 3.7 | 2.8-4.9 |
| | | sc | 12.7 | 10.7-15.0 |

Formulations:
A: 10% (v/v) DMSO, 10% (w/v) Beta hydroxy-propyl cyclodextrin (Sigma), 80% (v/v) of 5% (w/v) glucose in $H_2O$
B: 10% (v/v) DMSO, 40% (v/v) PEG 400 in 0.1 M aqueous $CH_3COOH$
C: 50% (v/v) PEG 400 in $H_2O$
Strains:
I. MSSA: Staph. aureus Smith 819 ATCC19636
II. MRSA: Staph. aureus 3817, clinical isolate
III. VanA: Ent. faecalis A533, clinical isolate, in neutropenic mice

BRIEF DESCRIPTION OF THE DRAWINGS

FIG. 8 represents the $^1$H-NMR spectrum of antibiotic 107891 Factor A1 recorded in the mixture $CD_3CN$:$D_2O$ (1:1) at 298 K on a Bruker AMX 600 spectrometer applying a water suppression sequence.

EXAMPLES

Example 1

Figure 1A:
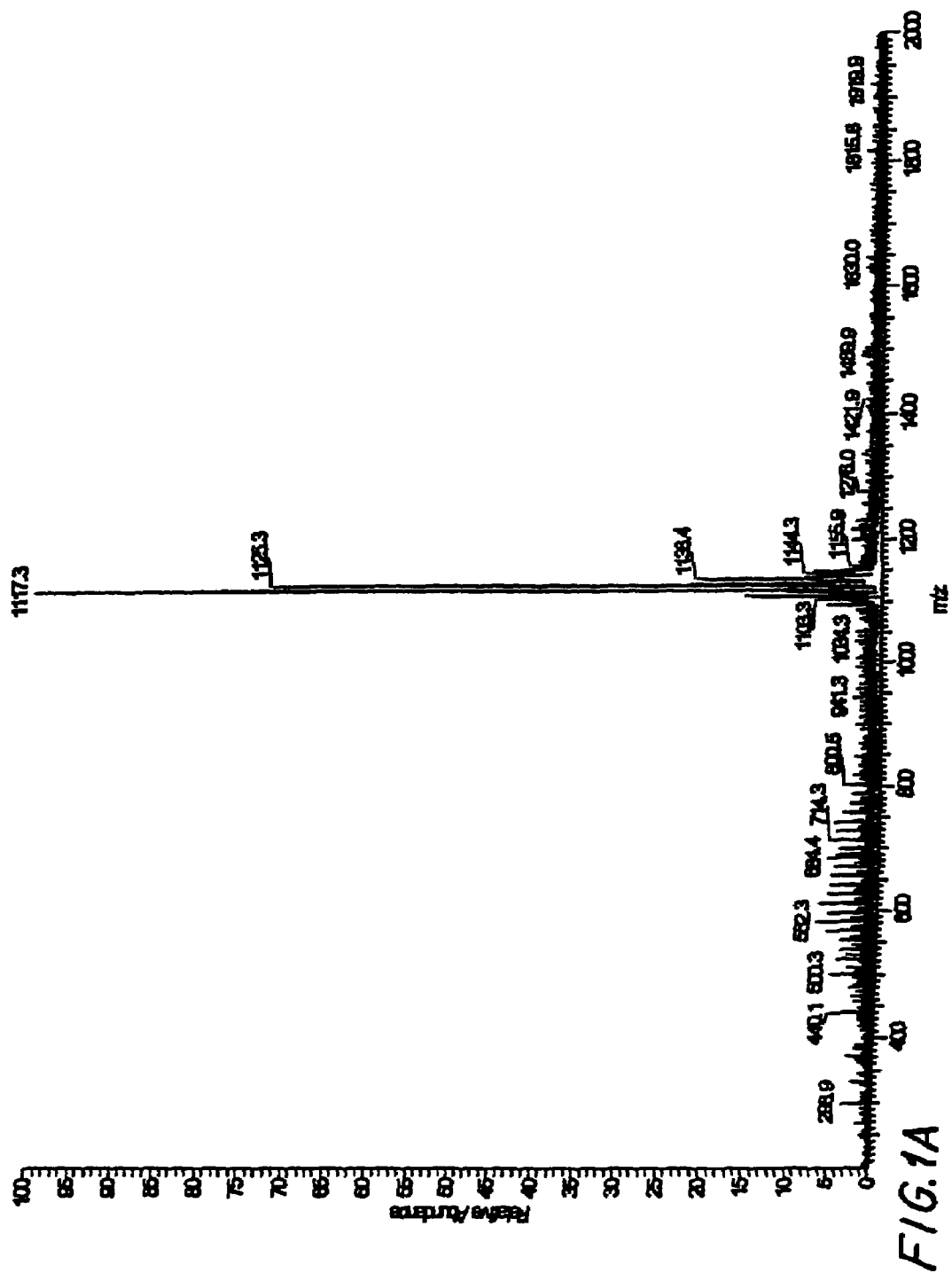
FIG. 1A (full scan low resolution spectrum) and 1B (zoom-scan high resolution spectrum) represent mass spectra of antibiotic 107891 showing a doubly protonated ion at m/z 1124 and m/z 1116.
Figure 1B:
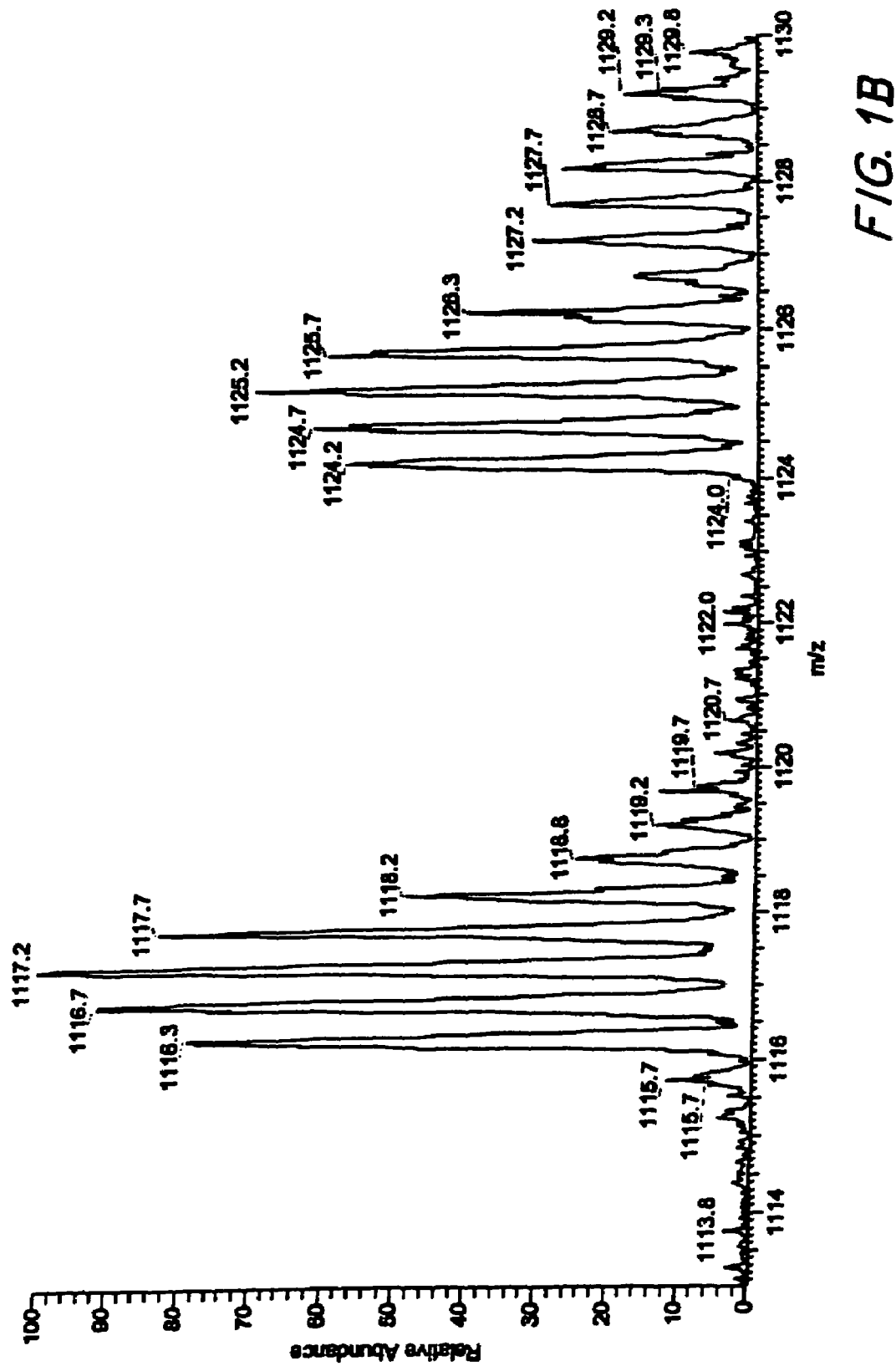
Figure 2:
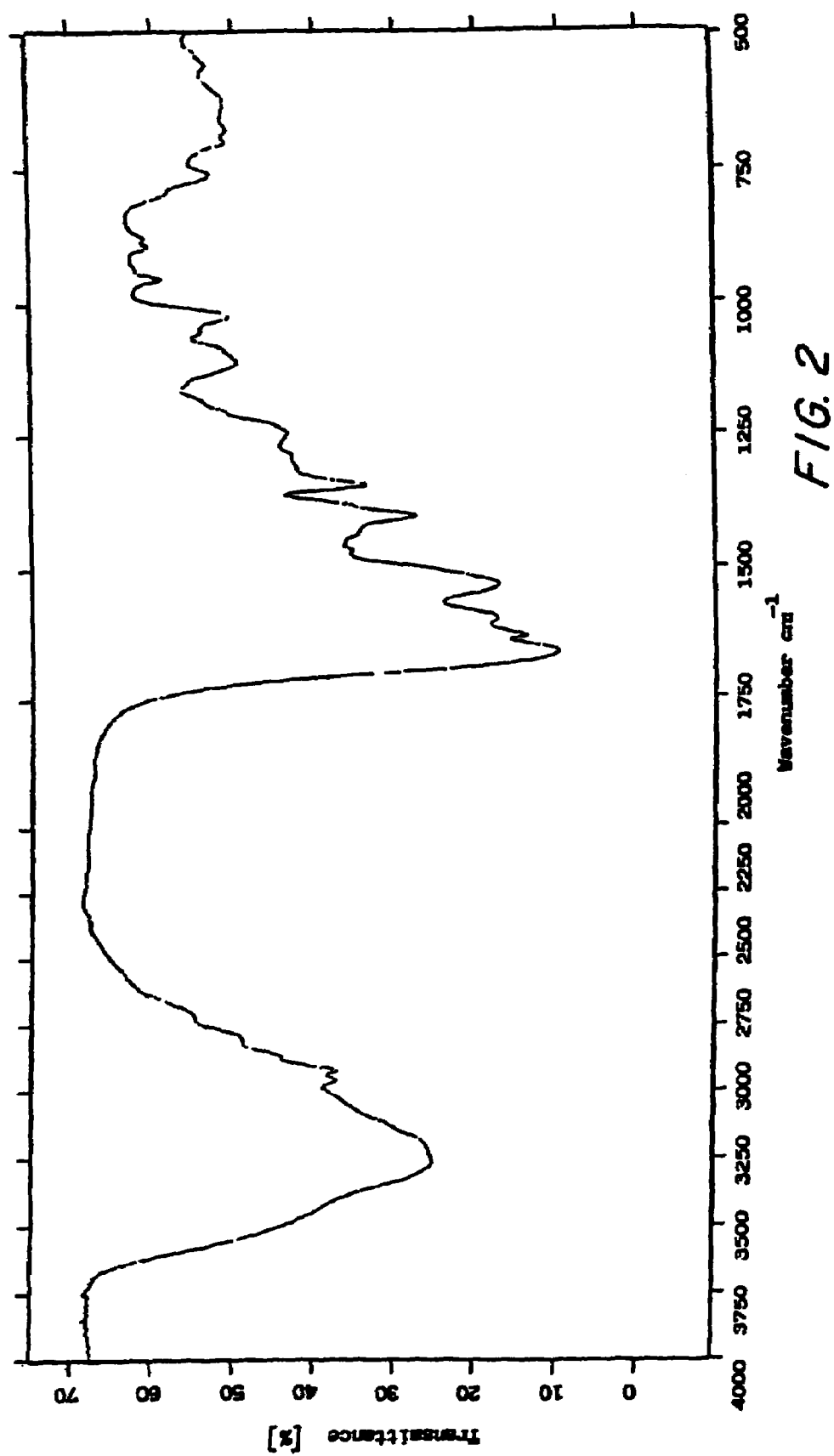
FIG. 2 represents the I.R. absorption spectrum of antibiotic 107891 dispersed in KBr.
Figure 3:
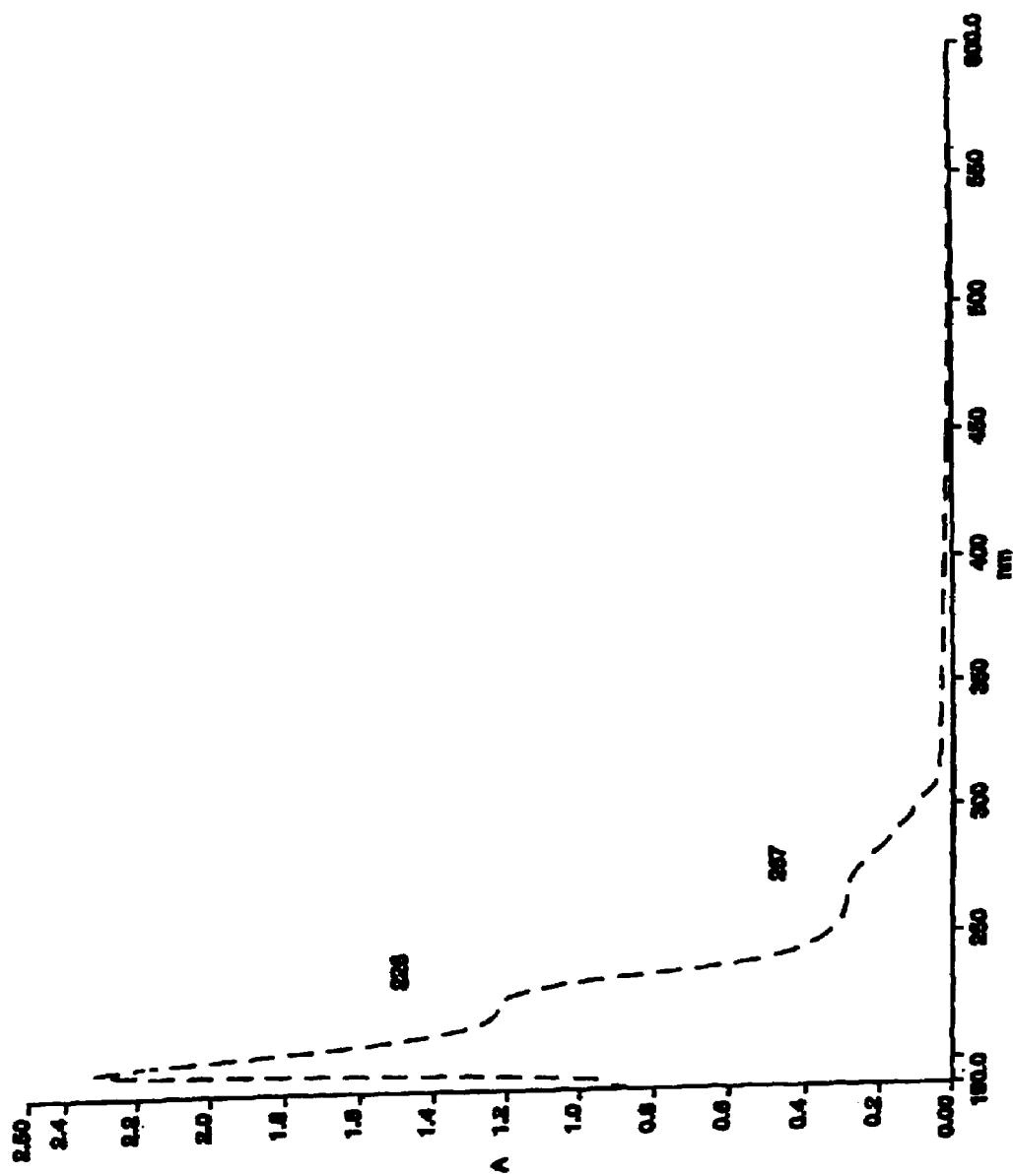
FIG. 3 represents the UV spectrum of antibiotic 107891 dissolved in methanol:$H_2O$.
Figure 4:
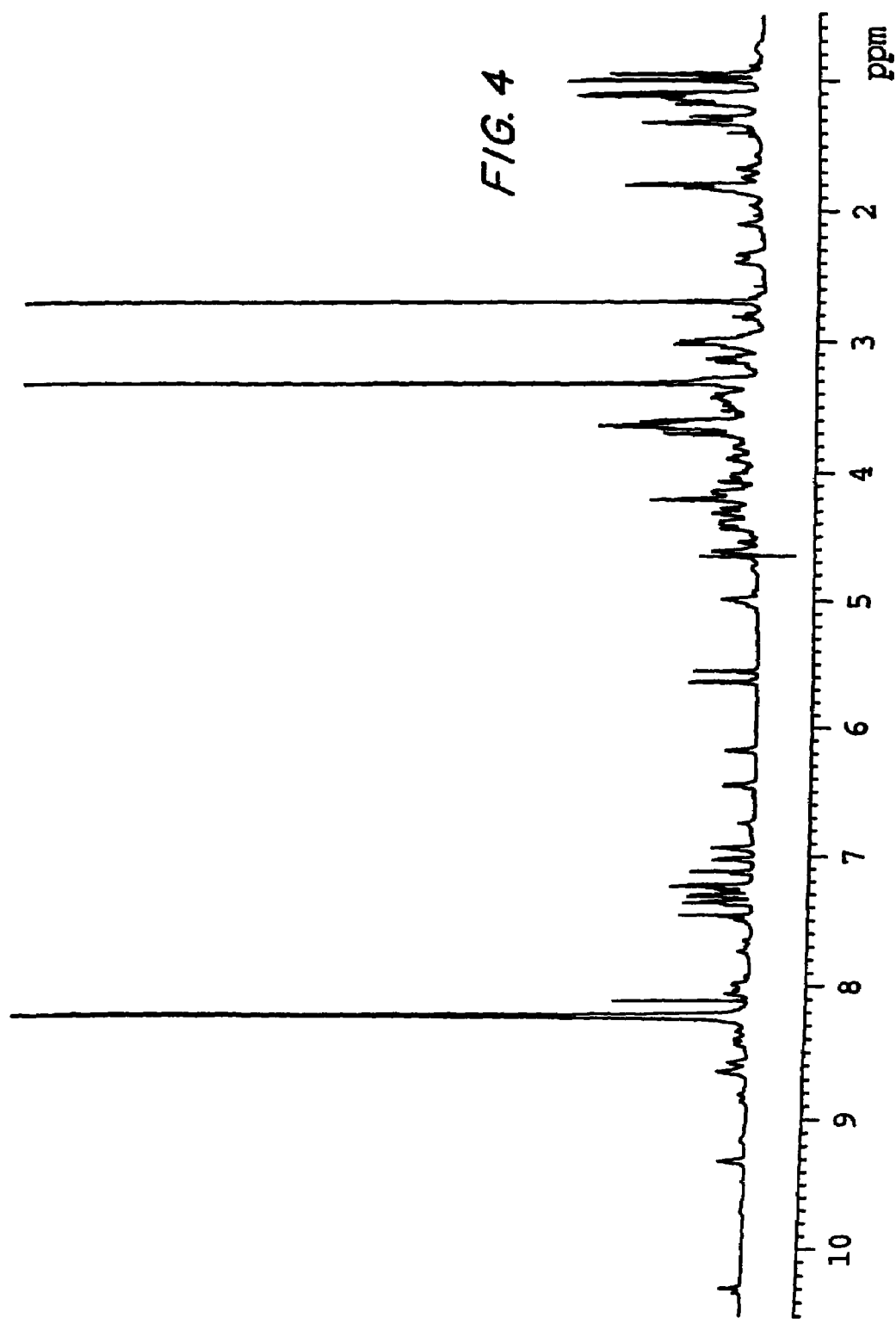
FIG. 4 represents the $^1$H-NMR spectrum recorded in the mixture methanol-d4:$H_2O$ (pH 4.3 HCl) 40:10 (v/v) at 40° C. on a Bruker AMX 600 spectrometer applying a water suppression sequence.
Figure 5:
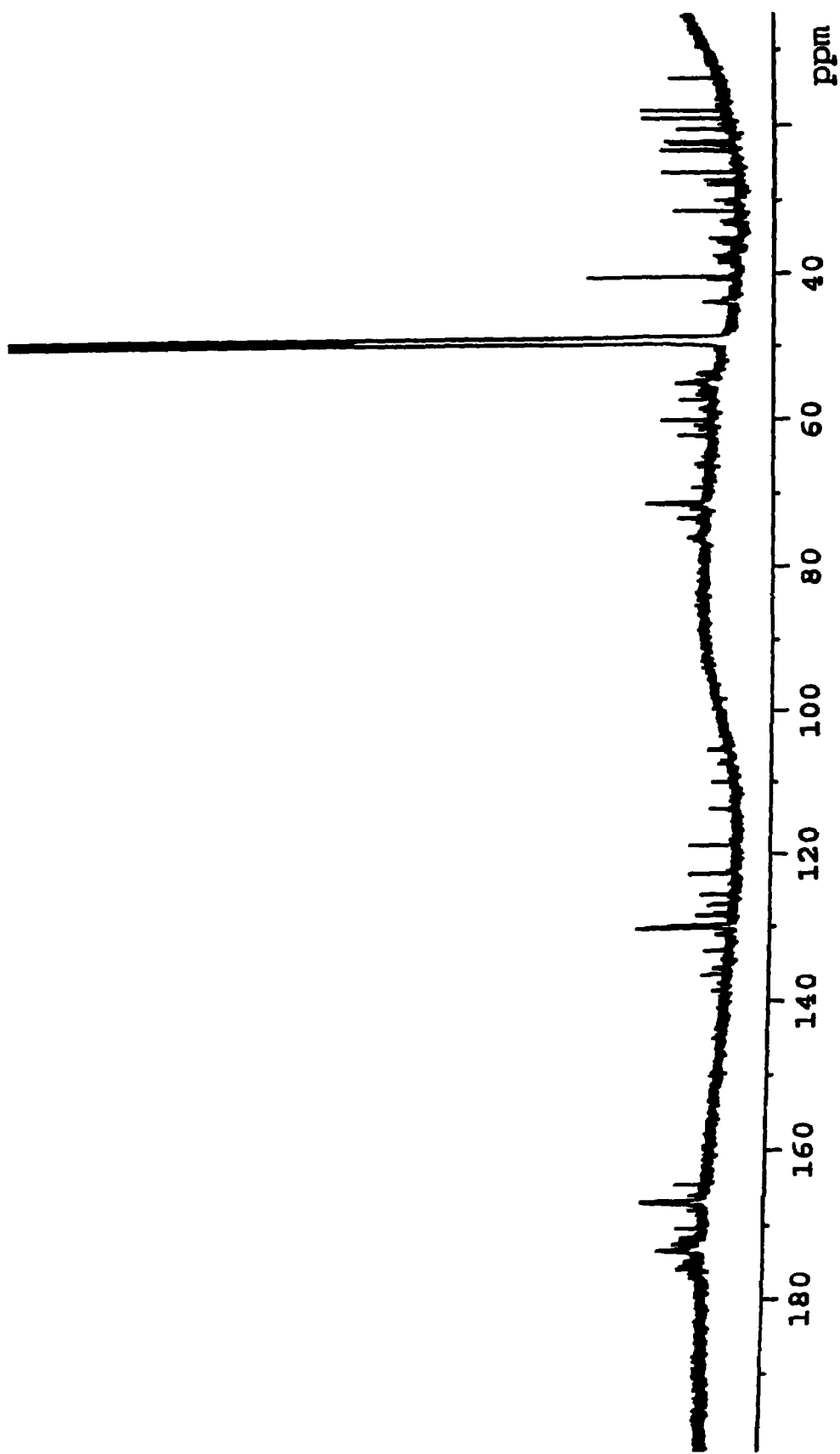
FIG. 5 represents the $^{13}$C-NMR spectrum recorded in the mixture methanol-d4:$H_2O$ (pH 4.3 HCl) 40:10 (v/v) at 40° C. on a Bruker AMX 600 spectrometer.
Figure 6A:
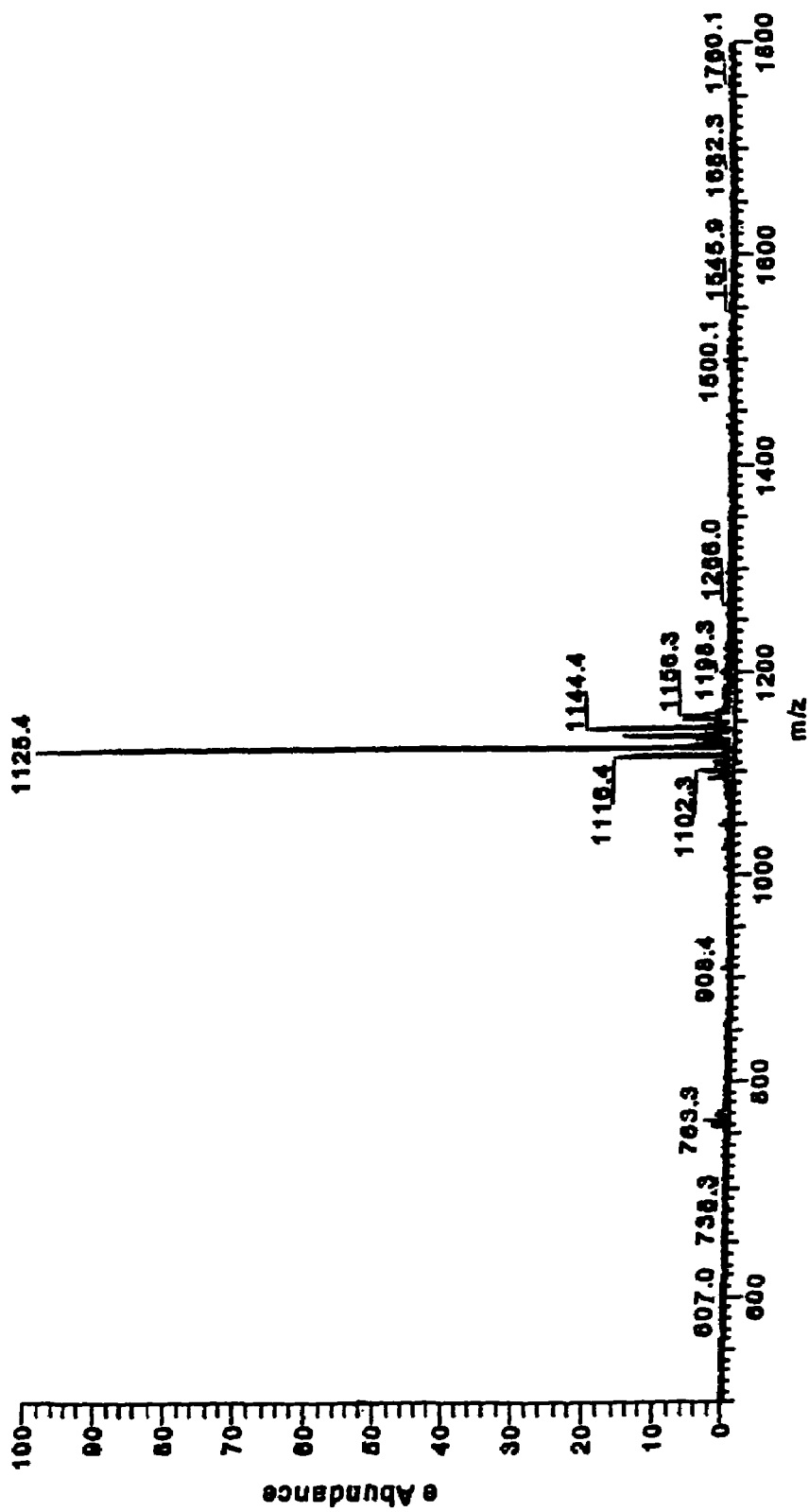
FIG. 6A (full scan low resolution spectrum) and 6B (zoom-scan high resolution spectrum) represent mass spectra of antibiotic 107891 Factor A1 showing a doubly protonated ions $[M+2H]^{2+}$ at m/z 1124.
Figure 6B:
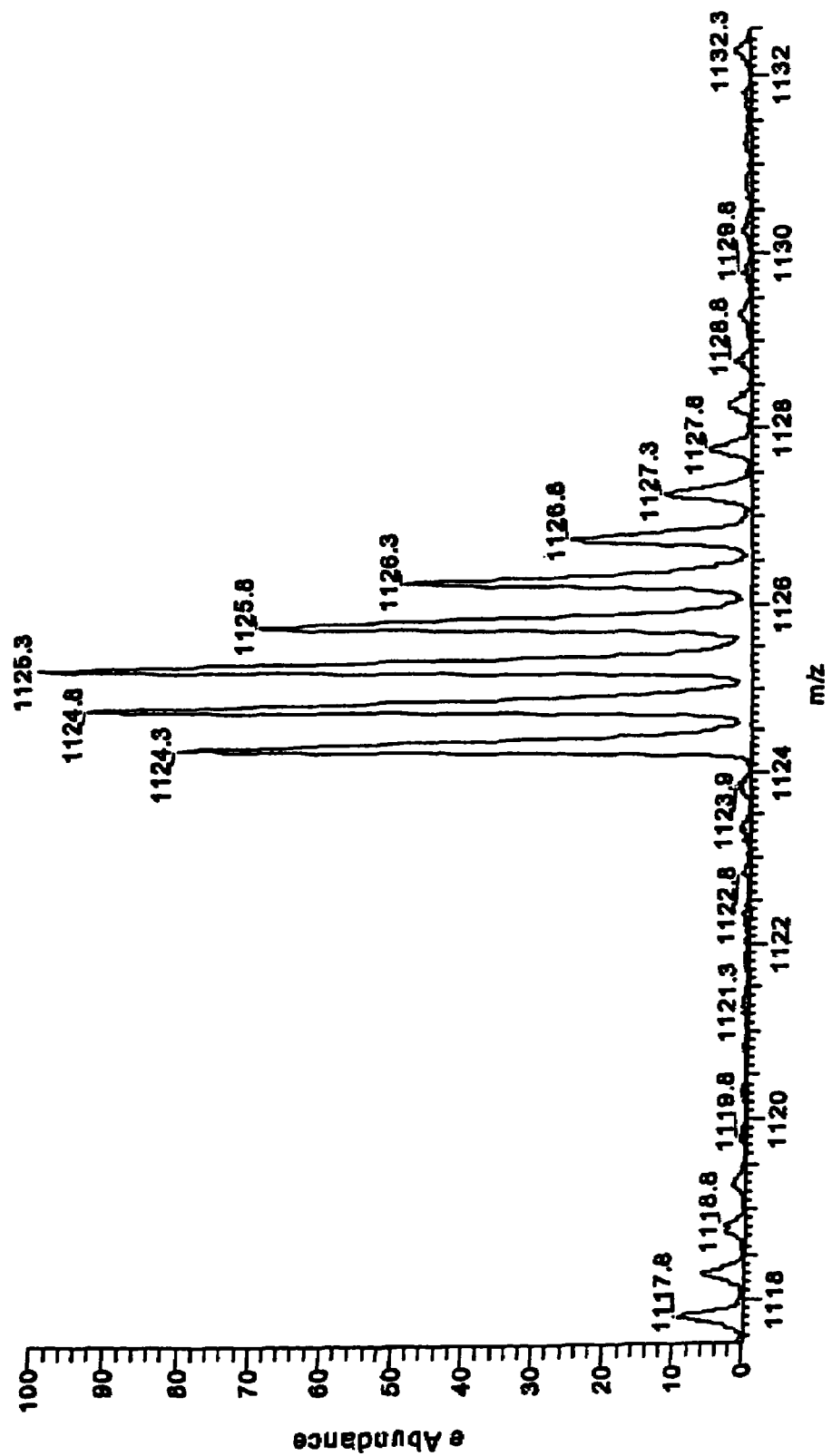
Figure 7A:
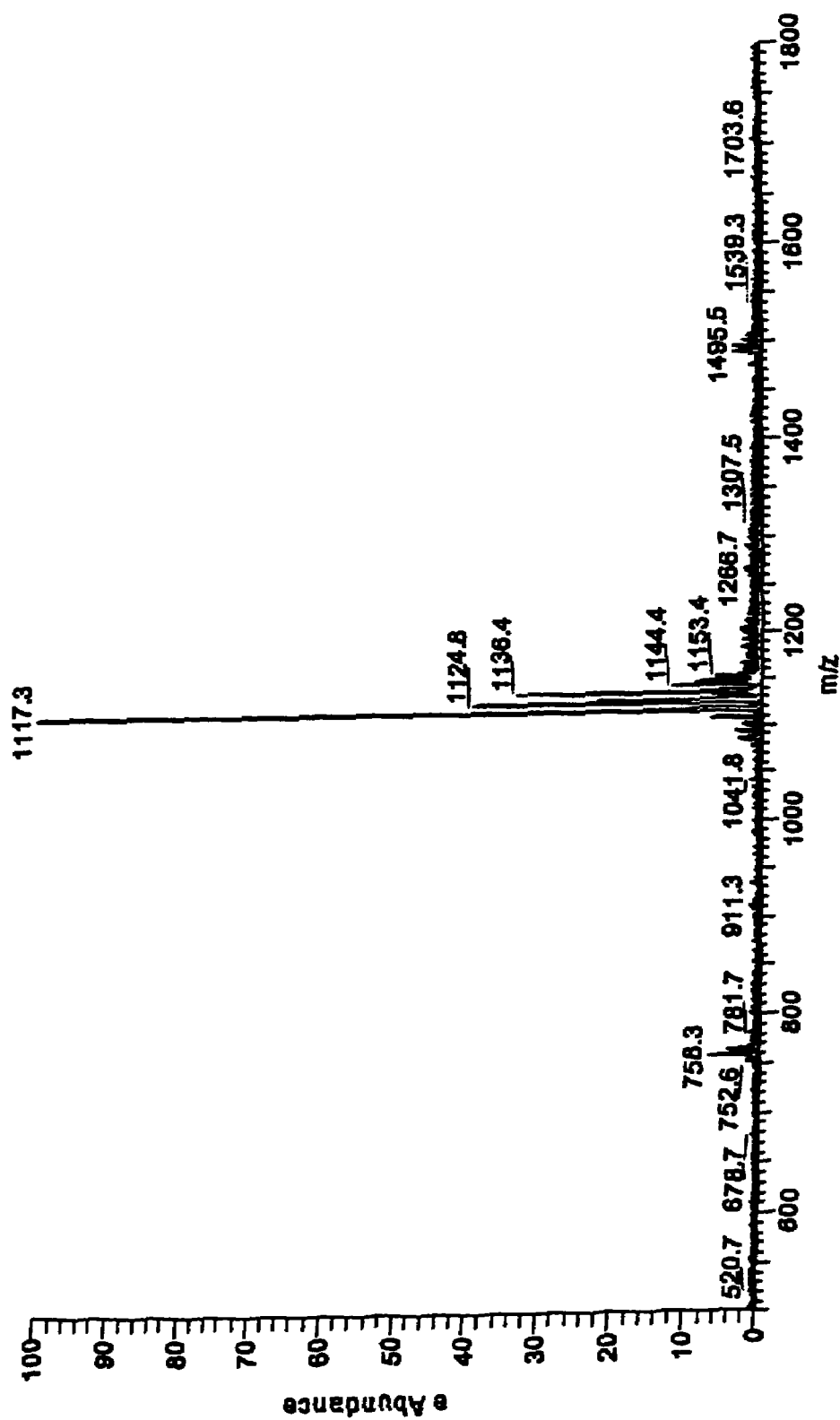
FIG. 7A (full scan low resolution spectrum) and 7B (zoom-scan high resolution spectrum) represent mass spectra of antibiotic 107891 Factor A2 showing a doubly protonated ions $[M+2H]^{2+}$ at m/z 1116.
Figure 7B:
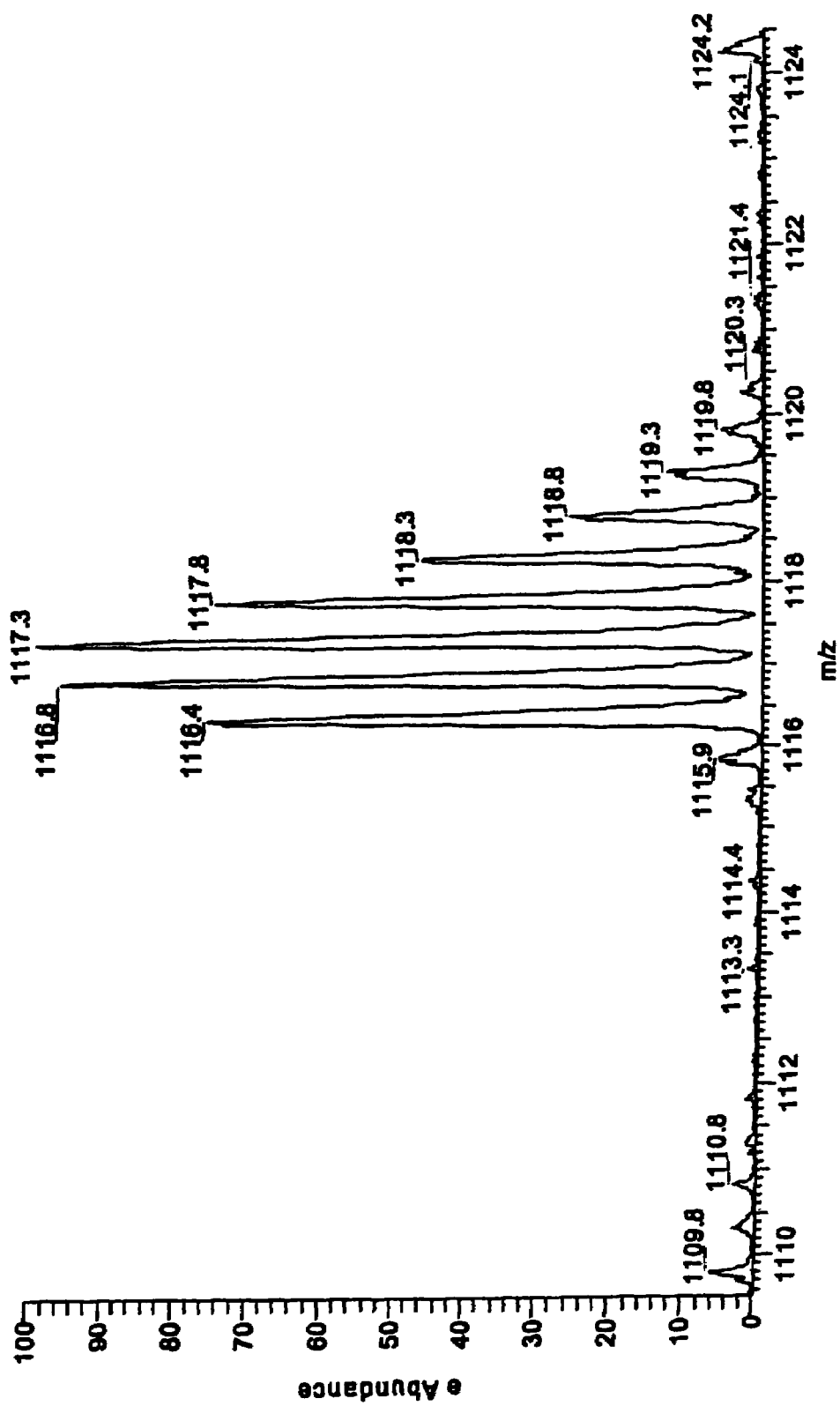
Figure 9:
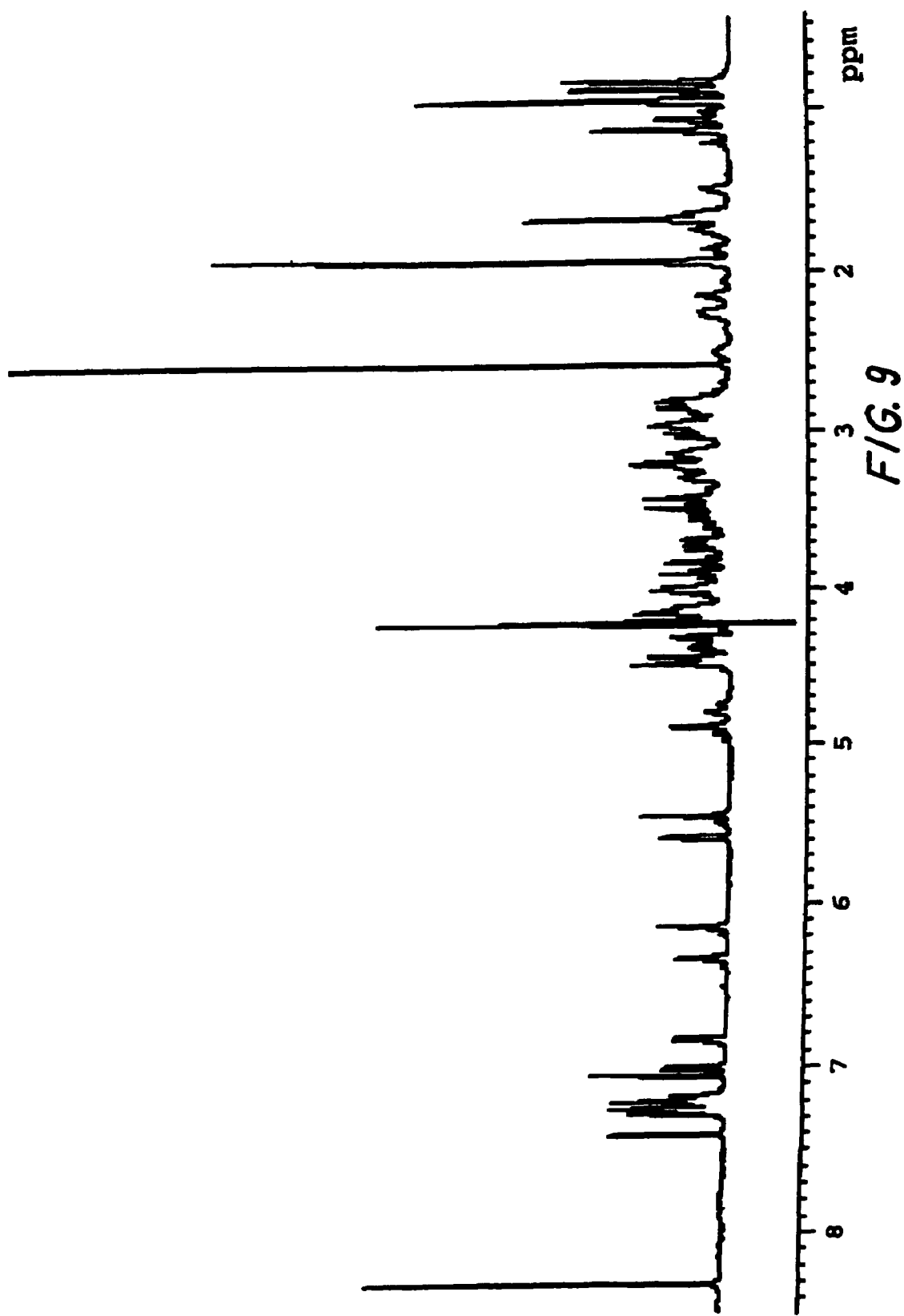
FIG. 9 represents the $^1$H-NMR spectrum of antibiotic 107891 Factor A2 recorded in the mixture $CD_3CN$:$D_2O$ (1:1) at 298 K on a Bruker AMX 600 spectrometer applying a water suppression sequence.
Figure 10:
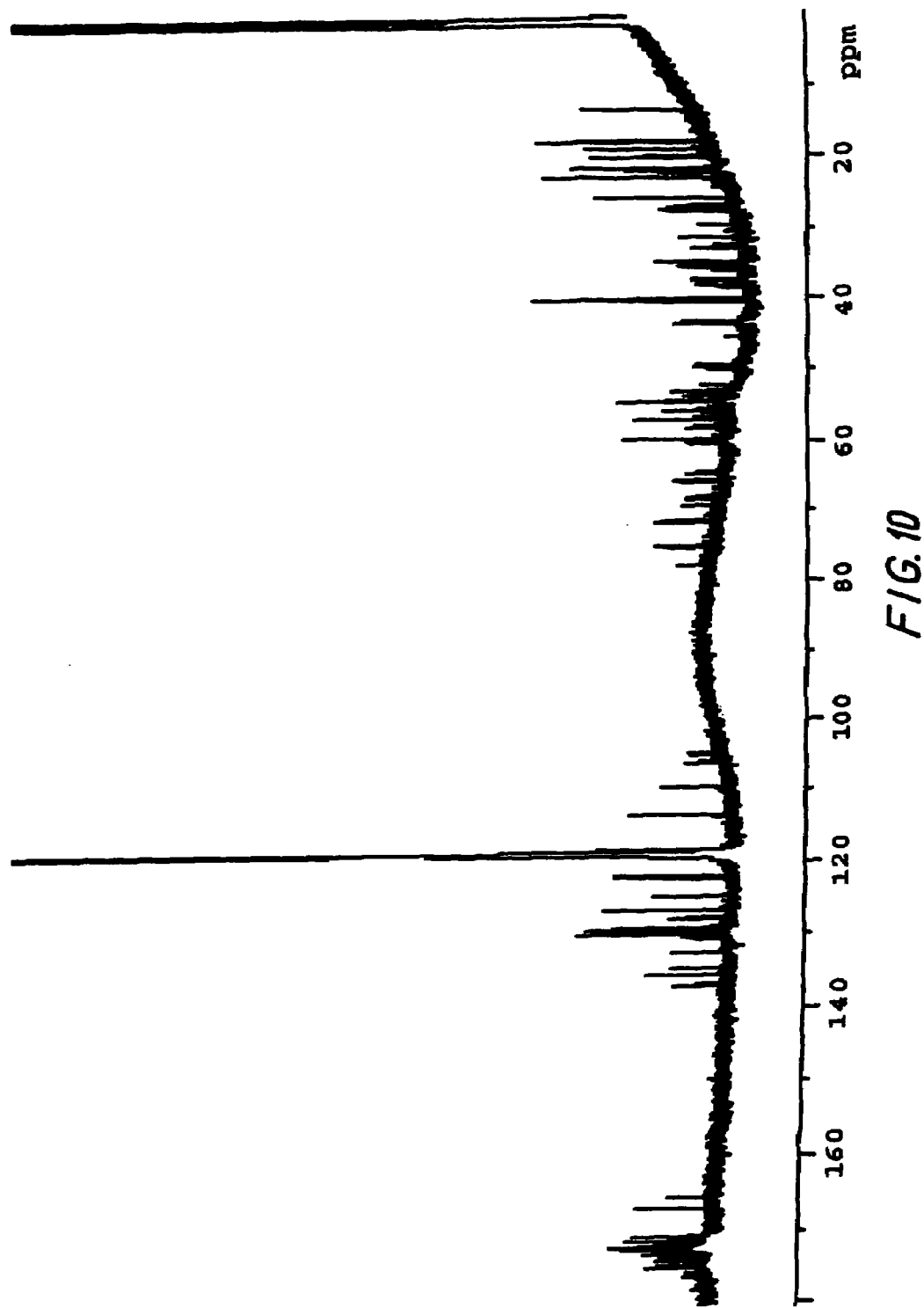
FIG. 10 represents the $^{13}$C-NMR spectrum of antibiotic 107891 Factor A1 recorded in the mixture $CD_3CN$:$D_2O$ (1:1) at 298 K on a Bruker AMX 600 spectrometer.
Figure 11:
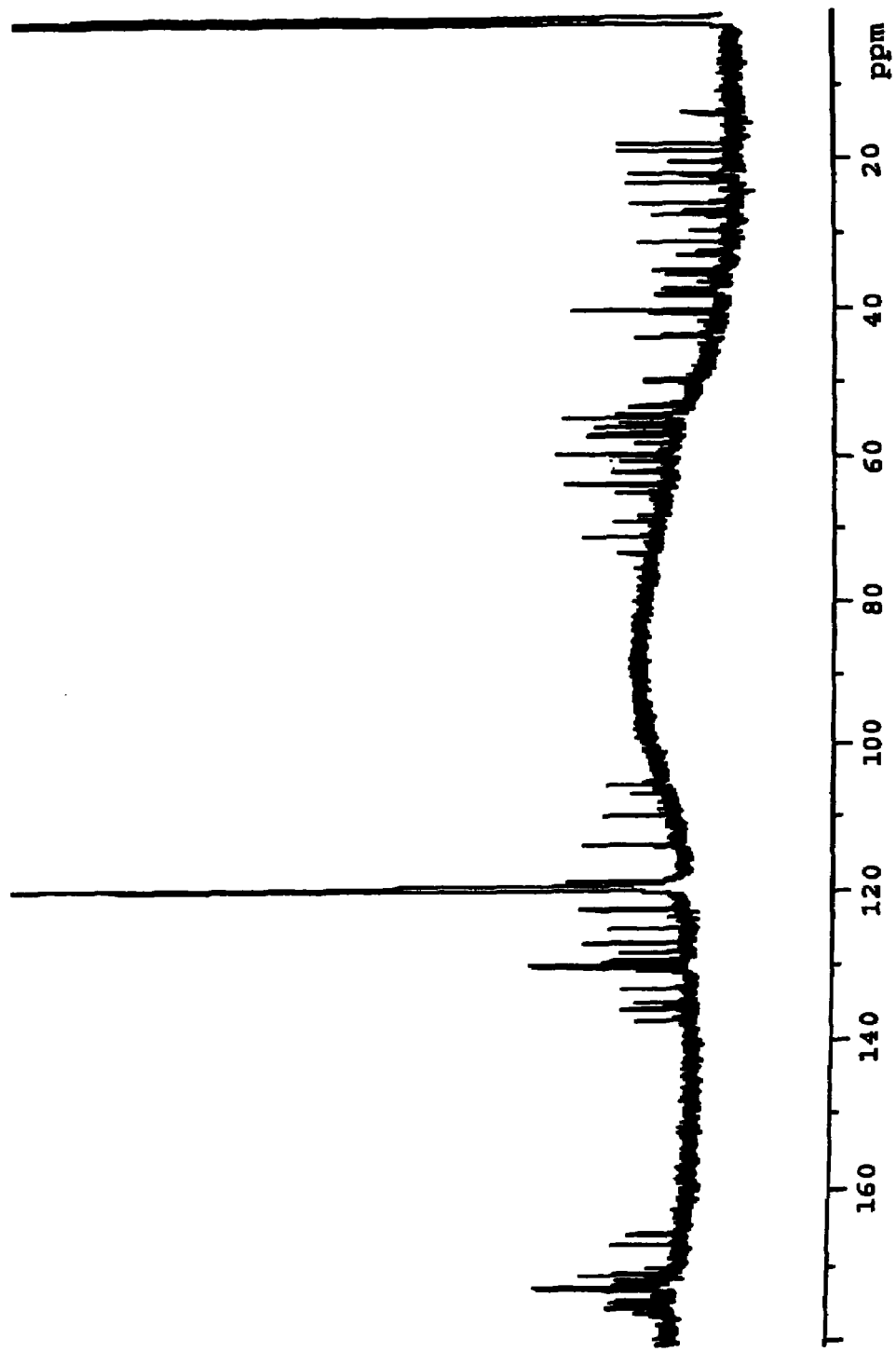
FIG. 11 represents the $^{13}$C-NMR spectrum of antibiotic 107891 Factor A2 recorded in the mixture $CD_3CN$:$D_2O$ (1:1) at 298 K on a Bruker AMX 600 spectrometer.
Figure 12:
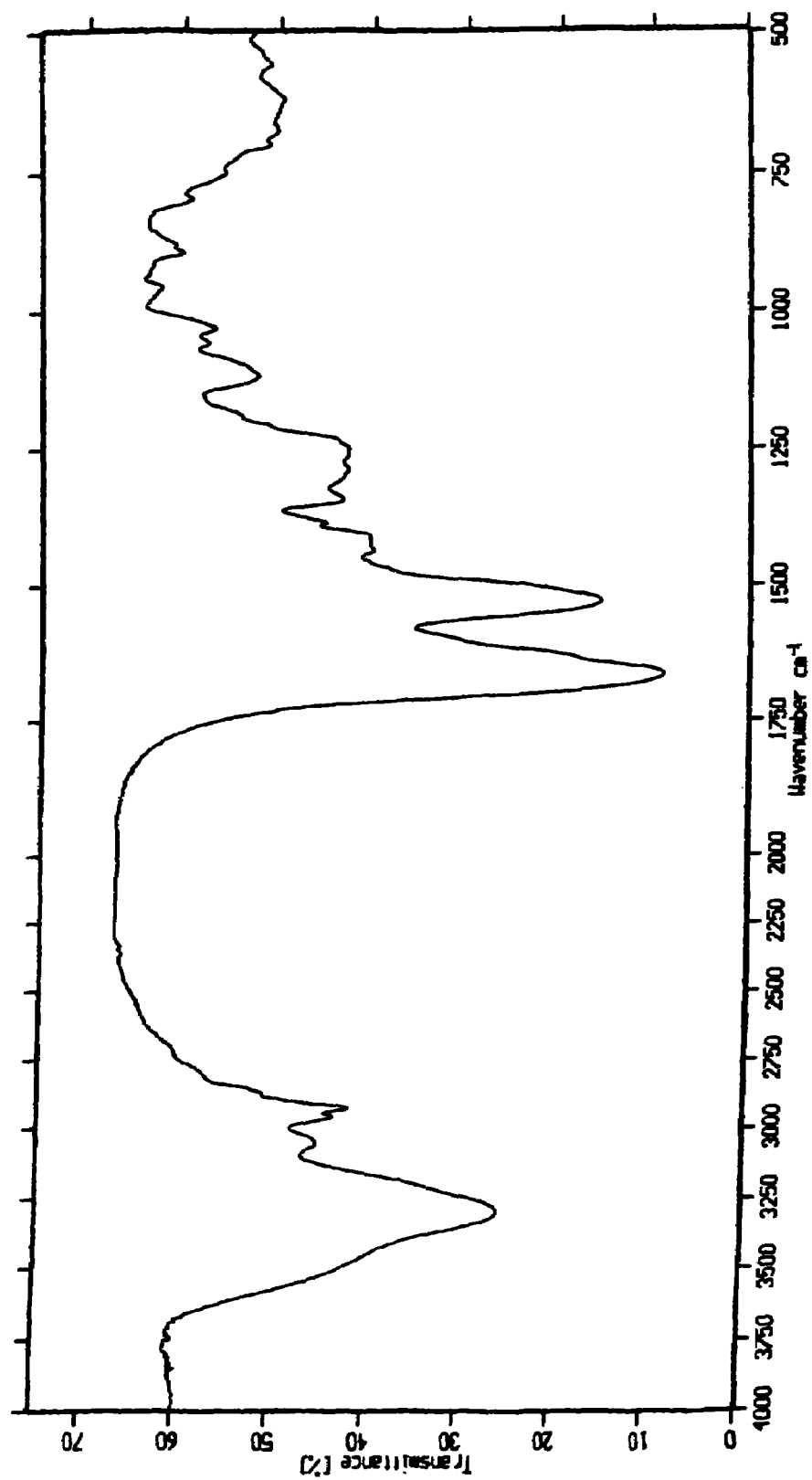
FIG. 12 represents the I.R. absorption spectrum of antibiotic 107891 Factor A1 dispersed in KBr.
Figure 13:
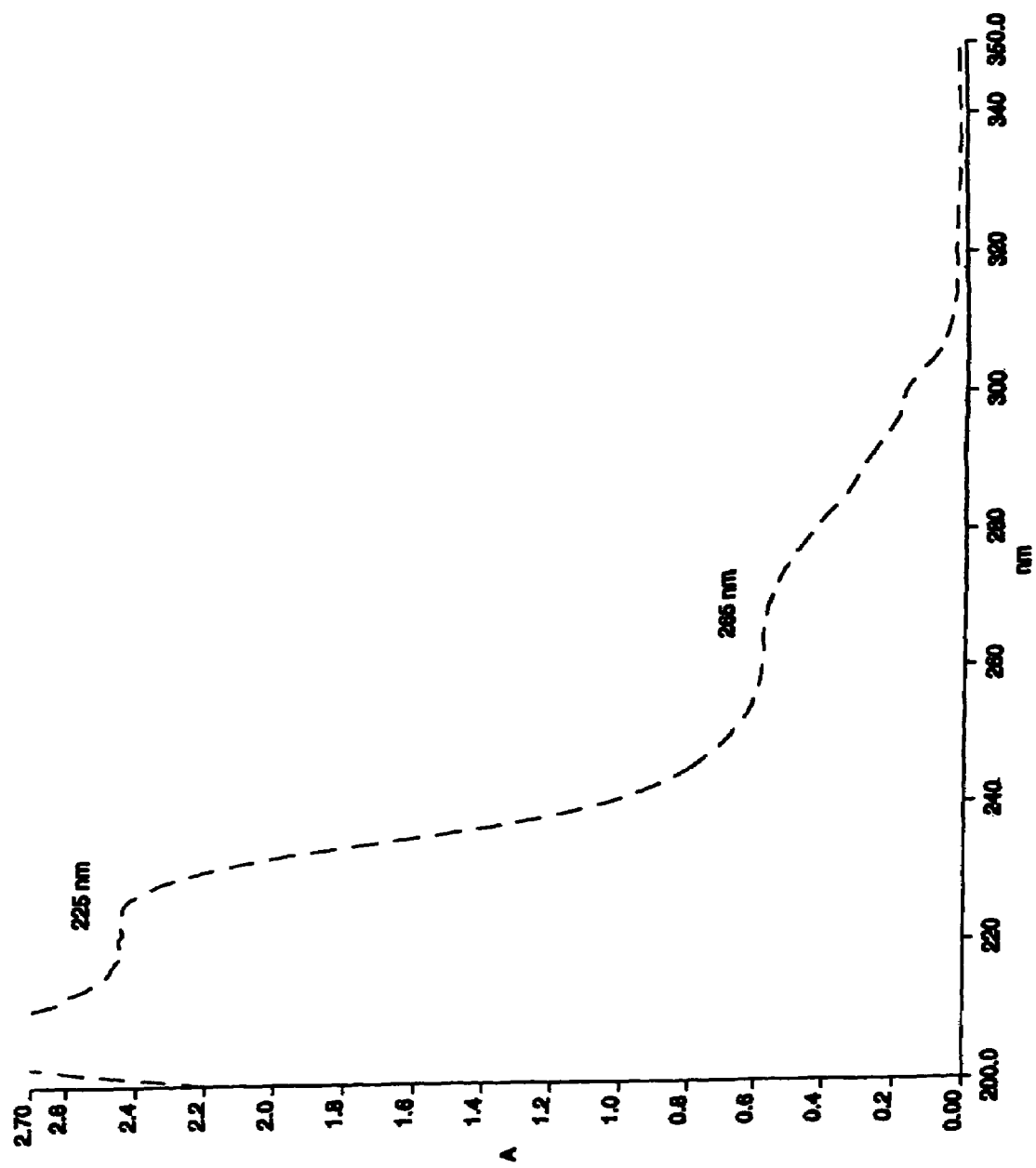
FIG. 13 represents the U.V. spectrum of antibiotic 107891 Factor A1 dissolved methanol:$H_2O$.
Figure 14:
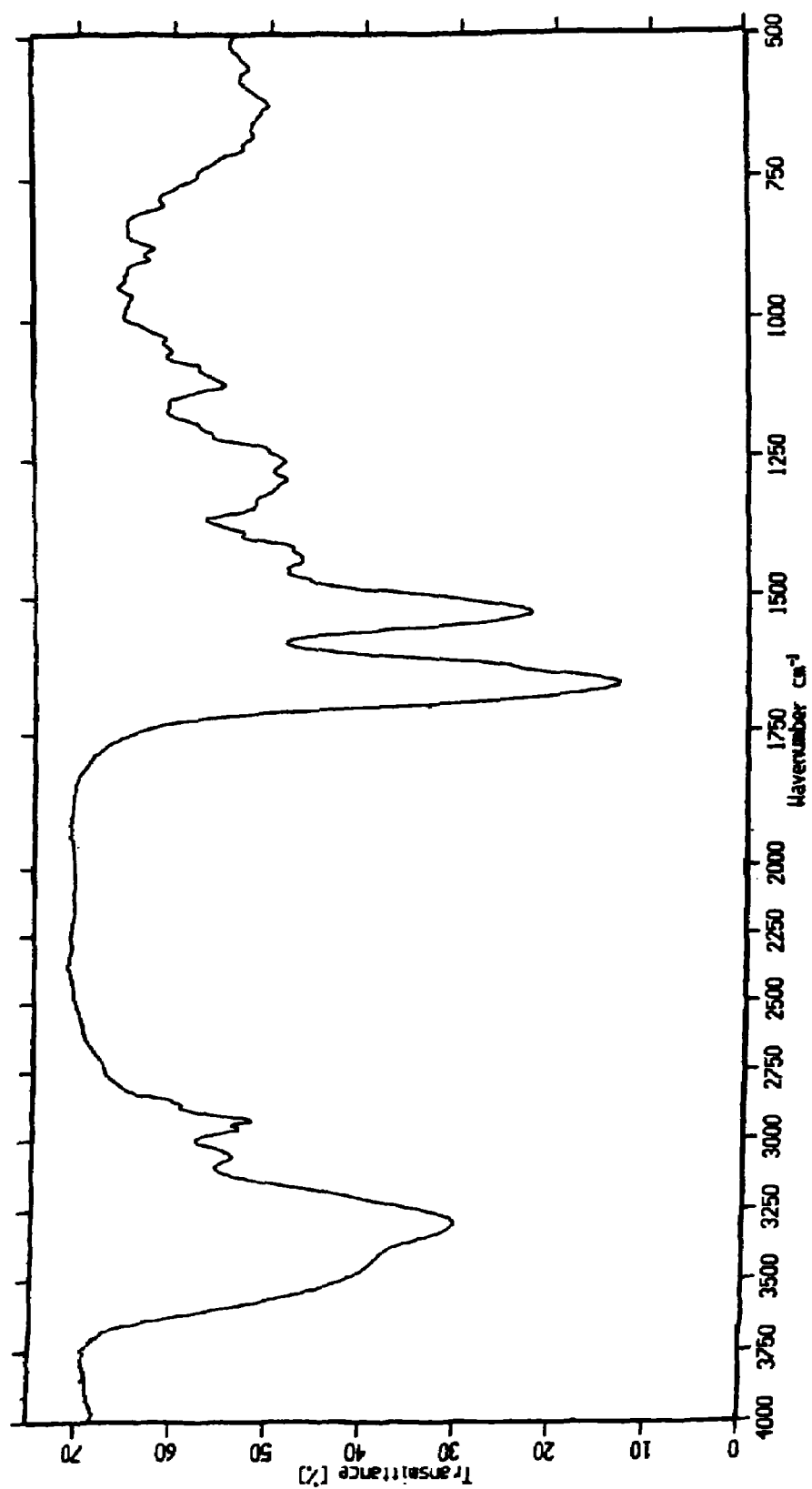
FIG. 14 represents the I.R. absorption spectrum of antibiotic 107891 Factor A2 dispersed in KBr.
Figure 15:
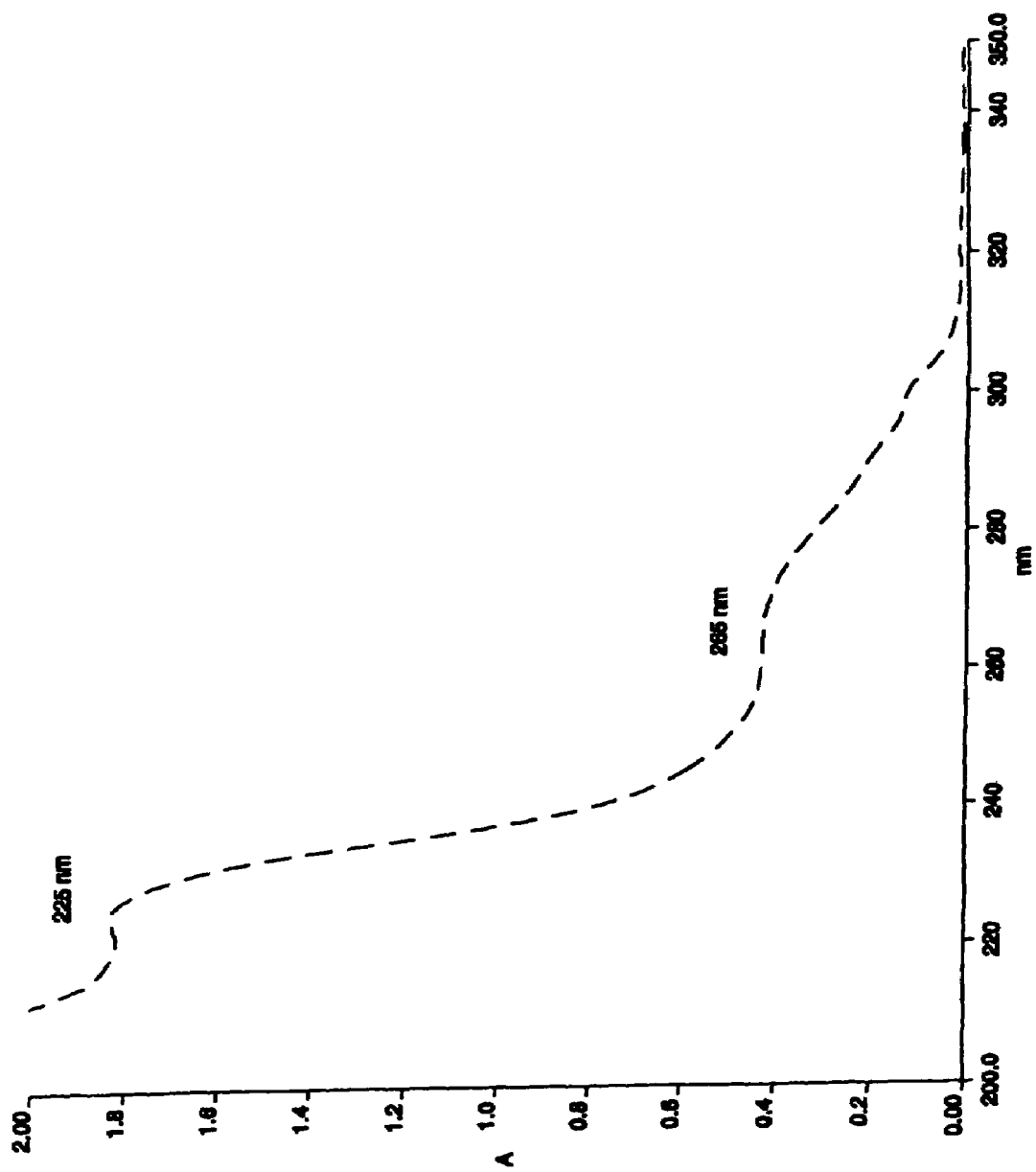
FIG. 15 represents the U.V. spectrum of antibiotic 107891 Factor A2 dissolved methanol:$H_2O$.

Fermentation Method of *Microbispora* sp. ATCC PTA-5024

*Microbispora* sp. ATCC PTA-5024 strain was maintained on oatmeal agar slants for 2-3 weeks at 28° C. The microbial content of one slant was scraped with 5 ml sterile water and inoculated into 500 ml Erlenmeyer flasks containing 100 ml of seed medium (AF/MS) which is composed of (g/l): dextrose 20, yeast extract 2, soybean meal 8, NaCl 1 and calcium carbonate 4. Medium was prepared in distilled water and pH adjusted to 7.3 prior to sterilization at 121° C. for 20 min. The inoculated flasks were grown at 28° C., on a rotatory shaker operating at 200 rpm. After 4-6 days, 5% of this culture was inoculated into a second series of flasks containing the same fermentation medium. After 72 hours of incubation, 200 ml were transferred into 4 l bioreactor containing 3 l of the same vegetative medium.

The fermentation was carried out at 30° C., with 700 rpm stirring and 0.5 vvm aeration. After 72 hours the culture (1.5 l) was transferred into a 20 l bioreactor containing 15 l of the same vegetative medium. The fermentation was carried out for 48 hours at 30° C., at 500 rpm stirring and at 0.5 vvm aeration and then was transferred to the production tank. The production of antibiotic 107891 was performed in a 300 l fermenter containing 200 l of the production medium M8 composed of (g/l): starch 20, glucose 10, yeast extract 2, casein hydrolysed 4, meat extract 2 and calcium carbonate 3. The medium was prepared in deionized water and the pH adjusted to 7.2 before sterilization at 121° C. for 25 min. After cooling the fermenter was inoculated with about 14 l (7%) of pre-culture. Fermenter was run at 29° C., at 180 rpm stirring and at 0.5 vvm aeration with a head pressure of 0.36 bar. The fermenter was harvested after 98 hours of fermentation.

The production of the antibiotic 107891 was monitored by HPLC as previously described, after extraction of the whole culture broth with the same volume of methanol. The extraction was performed at room temperature under stirring for one hour.

Example 2

Alternative Fermentation Method of *Microbispoza* sp. ATCC PTA-5024

*Microbispora* sp. ATCC PTA-5024 was inoculated in 500 ml Erlenmeyer flasks containing 100 ml of growing medium (G1) consisting of g/l: glucose 10, maltose 10, soybean oil 10, soybean meal 8, yeast extract 2 and calcium carbonate 4. The medium was prepared in deionised water and sterilized at 120° C.×20 min. without pH adjustment. The inoculated flasks were incubated for 120-168 hours at 28° C., under 200 rpm stirring till a good growth was observed. The flasks were then used to inoculate (3%) a 4 l bioreactor containing 3 l of seed medium AF/MS, which is composed as described in Example 1. After 120 hours of fermentation at 30° C., 700 rpm stirring and 0.5 vvm aeration, 1.5 l of the culture was transferred to a 20 l bioreactor containing 15 l of the same vegetative medium. The fermentation was carried out for 96 hours at 30° C., 600 rpm stirring and 0.5 vvm aeration, and was then transferred to the production tank.

The antibiotic production was obtained in a 300 l fermenter containing 200 l of the productive medium (V6) consisting of (g/l): dextrose 20, yeast extract 5, meat extract 5, hydrolysed casein 3, peptone 5 and NaCl 1.5. The medium was prepared in deionised water at pH adjusted to 7.5 with NaOH, and was sterilized at 121° C. for 20 min.

The fermenter was inoculated with 14 l of seed culture (7%) and the fermentation was carried out at 29° C., stirred at 180 rpm, aerated with 100 l of standard air per minute (0.5 vvm). The antibiotic 107891 production was monitored by HPLC as previously described. The fermentation was harvested after about 160 hours.

Example 3

Recovery of Antibiotic 107891

The fermentation broth described in the Example 1 was filtered by tangential filtration system (0.1 μm pore size membrane, Koch Carbo-Cor, Koch Wilmington, USA) to obtain 170 l of supernatant and 30 l of concentrated mycelium. Antibiotic 107891 complex was found both in the filtrate (A) and in the mycelium (B).

(A) The filtered broth was stirred one night at room temperature in the presence of Diaion HP-20 polystyrenic resin (4 l). The resin was then recovered, washed with 10 l methanol:water 4:6 (v/v) and eluted batchwise initially with 10 l methanol:water 9:1 (v/v) and then with 10 l methanol:butanol:water: 9:1:1 (v/v). The pooled eluted fractions containing antibiotic 107891 were concentrated to small volume on a rotary evaporator and then were freeze-dried, yielding 32 g of raw material. This raw material was dissolved in n-butanol (1 l) and then extracted three times sequentially with 800 ml water. The organic layer was concentrated under reduced pressure to an oily residue, which was dissolved in methanol. Upon addition of petroleum ether, 5 g of crude antibiotic preparation was obtained by precipitation.

(B) After addition of 25 l of methanol, the retentate portion containing the mycelium was stirred for 1 hour and was filtered to obtain 45 l of mycelium extract. This solution was then diluted with water (20 l) and was stirred one night at room temperature with Diaion HP-20 polystyrenic resin (1 l). The resin was then recovered, washed with 2 l methanol:water 40:60 (v/v) and eluted batch-wise sequentially with 3 l methanol:water 85:15 (v/v) and then with 2 l methanol:water 90:10 (v/v). The eluted fractions were monitored for the presence of antibiotic 107891 by agar diffusion assay on *Staphylococcus aureus* and by analytical HPLC method as previously reported.

The eluted fractions containing antibiotic 107891 were pooled, were concentrated under reduced pressure and were freeze dryed, yielding 8.1 grams of crude antibiotic 107891.

Example 4

Alternative Recovery of Antibiotic 107891

The harvested broth from the 200 l tank fermentation described in example 2 was brought to pH 6.8 and the broth was filtered by tangential filtration (0.1μ pore size membrane, Koch Carbo-Cor). The permeate (180 l) was stirred batch-wise overnight at room temperature with 2 l of Diaion HP20 resin (Mitsubishi Chemical) and the resin was then collected.

Methanol (25 l) was added to the retentate portion in the tangential filtration equipment (about 20 l) containing the concentrated mycelium. This suspension was stirred for 1 hour and then was filtered with the microfiltration system to a residual retentate volume of about 20 l. Additional methanol (25 l) was then added and the above process was repeated sequentially for a total of 5 cycles. The pooled methanol extracts (about 125 l) were diluted with 160 l of demineralized water and were stirred batch-wise overnight at room temperature with 3 l of Diaion HP 20 resin. The resin was then collected, and was pooled with the Diaion HP 20 resin used to extract the broth permeate according to the process above described. The pooled resin was washed into a chromatographic column with 20 l of water:methanol 6:4 (v/v). The antibiotic 107891 was eluted with 23 l of methanol: 50 mM ammonium formate buffer pH 3.5: n-butanol 9:1:1 (v/v). This eluate was then concentrated under vacuum to a final volume of 3 l. The concentrated solution was then loaded at pH 4.5 on a column of 2.5 l of polyamide CC 6 0.1-0.3 mm (Macherey-Nagel) conditioned with water:methanol 7:3 (v/v). The column was washed with water:methanol 7:3 (v/v) and then with 25 mM ammonium formate buffer pH 3.5: methanol 7:3 (v/v). The antibiotic was eluted with water:methanol 3:7 (v/v) and then with 1:9 (v/v) mixture. The elution was completed with 25 mM ammonium formate buffer pH 2.8: methanol in the ratio 1:9 (v/v). The eluates containing antibiotic 107891 were pooled and concentrated under vacuum to a final volume of 1 l. The pH of the concentrated solution was brought from 4 to 5.7 with 7 M ammonium hydroxide and then the mixture was centrifuged to collect the precipitate. This solid was suspended in water and freeze-dried, yielding 6.96 g of antibiotic 107891 preparation.

Example 5

Purification of Antibiotic 107891

Crude antibiotic 107891 (3.6 g), prepared as described in Example 3, was purified by medium pressure chromatography on 100 g of reverse phase C8 (EC) 40-70 μm particle size, 60A pore size, IST (International Sorbent Technology, Mid-Glamorgan, UK) by using a Bùchi B-680 Medium Pressure Chromatography System (Bùchi laboratoriumstechnik AG, Flawil Switzerland) equipped with B-687 gradient former, B-684 fraction collector, B-685 glass column 70×460 mm. The resin was previously conditioned with a mixture of phase A: phase B 8:2 (v/v) and was then eluted at 25 ml/min with 60 min linear gradient from 20% to 60% of phase B in 60 min.

Phase A was acetonitrile: 20 mM ammonium formate buffer (pH 6.6) 10:90 (v/v); and phase B was acetonitrile: 20 mM ammonium formate buffer (pH: 6.6) 90:10 (v/v).

The fractions containing antibiotic 107891 were pooled, concentrated under vacuum and lyophilized twice from water, yielding 430 mg of purified antibiotic 107891.

Example 6

Purification of Antibiotic 107891 by Preparative HPLC

Antibiotic 107891 was further purified by preparative HPLC on a Hibar prepacked lichrosorb RP8 (7:m particle size) column RT 250-25 mm, Merck, by using a 25 minutes linear gradient elution from 30% to 45% of Phase B, at 30 ml/min flow rate. Phase A was 25 mM ammonium formate buffer pH 4.5:acetonitrile 95:5 (v/v) and Phase B was acetonitrile.

A sample of Antibiotic 107891 from example 5 (300 mg) was dissolved in 1.5 ml 350:1 of DMSO:formic acid 95:5 (v/v) and 300 μl were processed per chromatographic run. Antibiotic 107891 was typically eluted in 15-16 minutes. The eluted fractions of 5 chromatographic runs, containing antibiotic 107891, were pooled and were concentrated under vacuum. The residual solution was lyophilised from water three times sequentially, yielding 31 mg of antibiotic 107891 as a white powder.

Example 7

Separation and Purification of Individual Factors A1 and A2 of Antibiotic 107891

Factors A1 and A2 were separated and purified from the antibiotic 107891 complex of Example 5 by preparative HPLC on a Symmetry Prep C18 (7 μm particle size) column 7.8×300 mm Waters (Mildfold USA) using two different elution programs.

A) Factor A1 was purified by a 25 minutes linear gradient elution from 30% to 45% of Phase B, at 3.5 ml flow rate. Phase A was 25 mM ammonium formate buffer pH 4.5: acetonitrile 95:5 (v/v) and Phase B was acetonitrile. Purified antibiotic 107891 complex (15 mg) was dissolved in 350 μl of DMSO:formic acid 95:5 (v/v) and was processed per chromatographic run. The A1 and A2 Factors were typically eluted in a 11-13 minutes time frame. The eluted fractions were then analysed by HPLC under the analytical conditions described above. The fractions of 14 chromatographic runs, containing pure antibiotic 107891 Factor A1, were pooled and were concentrated under vacuum. The residual solution was lyophilized from water three times sequentially, yielding 15 mg of pure Factor A1 as a white powder.

B) Factor A2 was purified by isocratic elution at 7 ml flow rate with 100 mM ammonium formate buffer pH 4:acetonitrile 82.5:17.5 (v/v). Purified antibiotic 107891 complex (5 mg) was dissolved in 250 μl of acetic acid:acetonitrile: 100 mM ammonium formate buffer pH 4 50:120:80 (v/v) mixture and was processed per chromatographic run. The A1 and A2 Factors were typically eluted in a 9-10 minutes time frame. The eluted fractions were then analysed by HPLC under the analytical conditions described above. The fractions of 20 chromatographic runs, containing pure antibiotic 107891 Factor A2, were pooled and were concentrated under vacuum. The residual solution was lyophilized twice from water yielding 8 mg of pure Factor A2 as a white powder.

The invention claimed is:

1. A compound, isolated from *Microbispora* sp. ATCC PTA-5042, of the formula

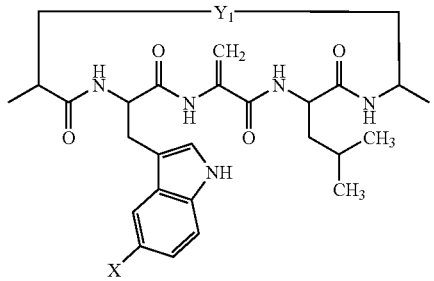

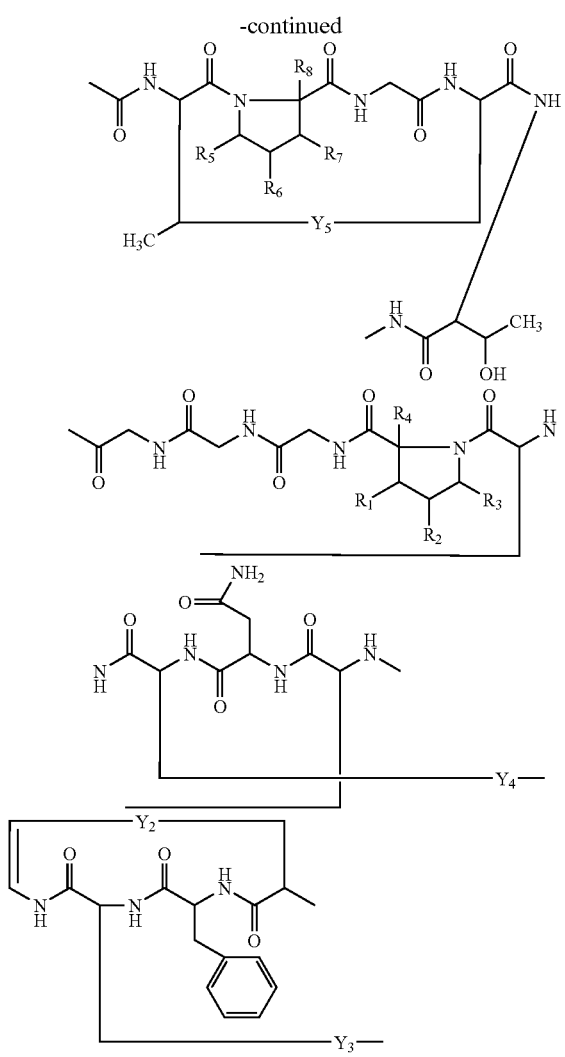

wherein X is selected from the group consisting of H, F, Cl, Br, and I; wherein $Y_1$, $Y_2$, $Y_3$, $Y_4$, and $Y_5$ are independently selected from the group consisting of S, S—O, S=O, O—S=O, and O=S=O; and wherein $R_1$, $R_2$, $R_3$, $R_4$, $R_5$, $R_6$, $R_7$, and $R_8$ are independently selected from the group consisting of H, OH, alkyl, and aryl.

2. The compound of claim 1, wherein $R_4$, $R_5$, $R_6$, $R_7$, and $R_8$ are H.

3. The compound of claim 2, wherein $R_1$ is H, $R_2$ is H, and $R_3$ is H.

4. The compound of claim 2, wherein $R_1$ is H, $R_2$ is H, and $R_3$ is OH.

5. The compound of claim 2, wherein $R_1$ is H, $R_2$ is OH, and $R_3$ is OH.

6. The compound of claim 2, wherein $R_1$ is OH, $R_2$ is OH, and $R_3$ is OH.

7. The compound of claim 2, wherein $R_1$ is OH, $R_2$ is H, and $R_3$ is H.

8. The compound of claim 2, wherein $R_1$ is OH, $R_2$ is H, and $R_3$ is OH.

9. The compound of claim 1, wherein $Y_1$ is selected from the group consisting of S—O, S=O, O—S=O, and O=S=O, and $Y_2$, $Y_3$, $Y_4$, and $Y_5$ are S.

10. The compound of claim 1, wherein $Y_2$ is selected from the group consisting of S—O, S=O, O—S=O, and O=S=O, and $Y_1$, $Y_3$, $Y_4$, and $Y_5$ are S.

11. The compound of claim 1, wherein $Y_3$ is selected from the group consisting of S—O.sup.-, S=O, O—S=O, and O=S=O, and $Y_1$, $Y_2$, $Y_4$, and $Y_5$ are S.

12. The compound of claim 1, wherein $Y_4$ is selected from the group consisting of S—O.sup.-, S=O, O—S=O, and O=S=O, and $Y_1$, $Y_2$, $Y_3$, and $Y_5$ are S.

13. The compound of claim 1, wherein $Y_5$ is selected from the group consisting of S—O.sup.-, S=O, O—S=O, and O=S=O, and $Y_1$, $Y_2$, $Y_3$, and $Y_4$ are S.

* * * * *